US012226760B2

(12) United States Patent
Hwang et al.

(10) Patent No.: US 12,226,760 B2
(45) Date of Patent: *Feb. 18, 2025

(54) MODIFIED METAL-ORGANIC FRAMEWORK AND CATALYST FOR HYDROGENATION REACTION INCLUDING SAME

(71) Applicant: KOREA RESEARCH INSTITUTE OF CHEMICAL TECHNOLOGY, Daejeon (KR)

(72) Inventors: Young Kyu Hwang, Daejeon (KR); Anil Haribhau Valekar, Daejeon (KR); Ma Eum Lee, Daejeon (KR); Kyung Ryul Oh, Daejeon (KR); Do Young Hong, Daejeon (KR)

(73) Assignee: KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 463 days.

This patent is subject to a terminal disclaimer.

(21) Appl. No.: 17/341,474

(22) Filed: Jun. 8, 2021

(65) Prior Publication Data

US 2022/0062880 A1 Mar. 3, 2022

(30) Foreign Application Priority Data

Jun. 9, 2020 (KR) ........................ 10-2020-0069898

(51) Int. Cl.

| | |
|---|---|
| ***B01J 31/16*** | (2006.01) |
| ***B01J 31/22*** | (2006.01) |
| ***B01J 37/00*** | (2006.01) |
| ***B01J 37/04*** | (2006.01) |
| ***B01J 37/06*** | (2006.01) |
| ***B01J 37/10*** | (2006.01) |
| ***C07C 29/141*** | (2006.01) |
| ***C07C 29/145*** | (2006.01) |
| ***C07C 37/055*** | (2006.01) |
| ***C07D 307/44*** | (2006.01) |
| ***C07D 307/58*** | (2006.01) |

(52) U.S. Cl.

CPC ....... *B01J 31/1691* (2013.01); *B01J 31/2213* (2013.01); *B01J 31/226* (2013.01); *B01J 31/2295* (2013.01); *B01J 37/009* (2013.01); *B01J 37/04* (2013.01); *B01J 37/06* (2013.01); *B01J 37/10* (2013.01); *C07C 29/141* (2013.01); *C07C 29/145* (2013.01); *C07C 37/055* (2013.01); *C07D 307/44* (2013.01); *C07D 307/58* (2013.01); *B01J 2231/643* (2013.01); *B01J 2531/48* (2013.01)

(58) Field of Classification Search

CPC .................................................... B01J 31/1691

See application file for complete search history.

(56) References Cited

U.S. PATENT DOCUMENTS

| | | | | |
|---|---|---|---|---|
| 10,195,592 B2 * | 2/2019 | Hwang | ................ | B01J 35/1023 |
| 2017/0320790 A1 * | 11/2017 | Hwang | .................. | B01J 37/036 |

FOREIGN PATENT DOCUMENTS

| | | |
|---|---|---|
| JP | 2010-42942 A | 2/2010 |
| KR | 10-2017-0124866 A | 11/2017 |
| KR | 10-1856709 B1 | 5/2018 |

OTHER PUBLICATIONS

[Supportive Materials for Exception to Loss of Novelty] Anil H. Valekar et al., "Catalytic Transfer Hydrogenation of Furfural to Furfuryl Alcohol under Mild Conditions over Zr-MOFs: Exploring the Role of Metal Node Coordination and Modification," ACS Catalysis, Feb. 3, 2020, pp. 3720-3732, vol. 10.

Office Action issued on Nov. 13, 2021, for corresponding Korean Patent Application No. 10-2020-0069898, along with an English translation.

Dong Yang et al., "Tuning Catalytic Sites on Zr6O8 Metal-Organic Framework Nodes via Ligand and Defect Chemistry Probed with tert-Butyl Alcohol Dehydration to Isobutylene", Journal of the American Chemical Society (JACS), Apr. 5, 2020, vol. 142, p. 8044~8056 , cited in NPL No. 1.

* cited by examiner

*Primary Examiner* — Shawquia Jackson

(74) *Attorney, Agent, or Firm* — Hauptman Ham, LLP

(57) ABSTRACT

The present disclosure relates to a metal-organic framework modified using a compound having a hydroxyl group (—OH), a catalyst for a hydrogenation reaction including the same, and a method of manufacturing the same. The catalyst according to the present disclosure has high activity to the hydrogenation reaction even at a low temperature of 30 to 40° C., thus making low-grade waste heat usable.

10 Claims, 22 Drawing Sheets

MODIFIED METAL-ORGANIC FRAMEWORK AND CATALYST FOR HYDROGENATION REACTION INCLUDING SAME

CROSS REFERENCE TO RELATED APPLICATION

The present application claims priority based on Korean Patent Application No. 10-2020-0069898, filed on Jun. 9, 2020, the entire content of which is incorporated herein for all purposes by this reference.

BACKGROUND OF THE DISCLOSURE

1. Field of the Disclosure

The present disclosure relates to a modified metal-organic framework and a catalyst for a hydrogenation reaction including the same. Specifically, the metal-organic framework is modified with a compound having a hydroxy (—OH) group such as methanol to improve catalytic activity for a hydrogenation reaction.

2. Description of the Related Art

According to the demand for energy to overcome environmental deterioration and the gradual depletion of fossil resources and to improve the quality of life, research on alternative renewable resources is in progress. Among the few renewable resources, only some types of biomass, which are abundant in nature and inexpensive, are sustainable sources of chemical materials typically derived from liquid fuels and fossil resources. A great deal of effort is required to develop catalytic processes suitable for the production of various platforms and value-added chemical materials either directly from lignocellulosic biomass or from carbohydrates. Among the chemical materials, GVL (γ-valerolactone) is recognized as a versatile building block, and may be used as an additive to liquid fuel in transportation, as a precursor for manufacturing polymerizable monomers, and as a precursor for synthesizing various value-added chemical materials including organic solvents and bio-oxygenates. The GVL is excellent as a green solvent for biomass treatment because of excellent physical and chemical properties thereof such as a low melting point and a high boiling point, a very low vapor pressure even at high temperatures, and immediate miscibility with water without forming an azeotropic mixture.

In general, three main strategies have been developed for the production of GVL from levulinic acid (LA) and esters of LA depending on the variety of hydrogen sources. Hydrogen molecules ($H_2$) are the most common hydrogen source used in this reaction, and the reaction occurs in the presence of various metal catalysts (for example, Ru, Pt, Pd, Ni, Co, and Cu). Further, formic acid (FA) is formed in the same molar amount as LA during acid hydrolysis of carbohydrates, and is also used as a hydrogen source to produce GVL from LA, thereby realizing the principle of atom economy. Several catalyst systems including nickel-promoted copper-silica and Ag—Ni—$ZrO_2$ nanocomposites have been successfully used to convert LA into the same molar amount of GVL while consuming the same molar amount of FA as a hydrogen donor. However, the two hydrogenation strategies described above have a limitation in a somewhat large scale application due to several limitations (for example, harsh reaction conditions, use of corrosive acids, and use of precious metals and non-environmentally friendly solvents).

Recently, the document by Dumesic et al., for the first time, reported a hydrogenation reaction method using a catalyst based on the MPV (Meerwein-Ponndorf-Verley) reduction principle of using a secondary alcohol as a hydrogen donor and hydrogenating LA and alkyl levulinate to GVL under a heterogeneous catalyst. In the document, it was demonstrated that $ZrO_2$ has better activity than other metal oxides due to the amphoteric nature thereof. The chemical selectivity of the MPV reduction reaction of aldehydes and ketones to carbonyl groups, the replacement of hydrogen molecules with alcohols, and the effective performance of non-precious metal-containing catalysts provide a cost-effective alternative to the manufacture of GVL. Therefore, various zirconium-based catalyst systems such as $ZrO_2$, $ZrO(OH)_2$, and amorphous Zr-complexes [zirconium 4-hydroxybenzoate (Zr-HBA) and zirconium phosphonate (Zr-PhyA)] have been mainly reported for the above-described reaction within a short period of time.

Korean Patent No. 10-1856709 (2018.05.10) relates to a MOF-808-based catalyst for a transfer hydrogenation reaction, and shows that a catalytic transfer hydrogenation reaction of levulinic acid (LA) to gamma-valerolactone (GVL) is capable of being performed under a relatively mild condition using the MOF-808-based catalyst.

However, the prior document shows that the reaction is at a low reaction capable of being performed even temperature, but does not mention that the reaction is performed to a practical extent at a temperature of 30 to 40° C., which is close to room temperature, without maintaining a high-pressure reaction state.

CITATION LIST

Patent Literature (Patent Document 001) Korean Patent No. 10-1856709 (2018.05.10.)

SUMMARY OF THE DISCLOSURE

Accordingly, an objective of the present disclosure is to provide a modified metal-organic framework exhibiting catalytic activity even at low temperatures so as to be applicable even to low-grade waste heat in production of biomass-derived chemical materials.

Another objective of the present disclosure is to provide a catalyst for a hydrogenation reaction having a local structure including a modified metal-organic framework.

In order to accomplish the above objectives, the present disclosure provides a modified metal-organic framework which is modified using a compound having a hydroxyl group (—OH).

The metal-organic framework may be at least one selected from among MOF-808, PCN-700, PCN-777, PCN-222, PCN-225, NU-902, NU-901, NU-1000, NU-1200, BUT-12, DUT-51, MOF-545, MMPF-6, MOF-841, and hcp UiO-66.

In an embodiment, the metal-organic framework may be represented by the following Chemical Formula 1 or Chemical Formula 2.

$$M_6O_{4+x}(OH)_m(BTC)_2(OR)_n \quad \text{[Chemical Formula 1]}$$

(M is a Group 4A or 4B element on a periodic table or a lanthanide-based metal having an oxidation state of $4^+$, x is greater than 0, a sum of m and n is 10 or less, m is greater than n, and R is an alkyl group having 1 to 10 carbon atoms)

$M_6(\mu_3\text{-}O)_4(\mu_3\text{-}OH)_4(OH)_x(H_2O)_6(BTC)_2(OR)_y$ [Chemical Formula 2]

(x is any number greater than 0 and less than or equal to 12, y is any number from 0 to 6, M is a Group 4A or 4B element or a lanthanide-based metal having an oxidation state of $4^+$, and R is an alkyl group having 1 to 10 carbon atoms)

Further, in an embodiment of the present disclosure, the compound having the hydroxyl group may be at least one selected from among methanol, ethanol, and propanol.

The present disclosure also provides a catalyst for a hydrogenation reaction, which includes the modified metal-organic framework.

In an embodiment of the present disclosure, the metal-organic framework may have a metal node coordination number of 10 or less.

For another objective of the present disclosure, the present disclosure provides a method of manufacturing a catalyst for a hydrogenation reaction. The method includes immersing a metal-organic framework in a compound having a hydroxyl group a to manufacture mixture, performing refluxing while heating the mixture to or above a boiling point of the compound having the hydroxyl group, and performing filtering, washing, and drying. The compound having the hydroxyl group may be methanol.

The present disclosure also provides a method of producing a reduced organic compound, the method including performing a hydrogenation reaction between a substrate and a hydrogen donor using the hydrogenation catalyst according to the present disclosure.

In an embodiment, the substrate may be a compound having a C═O bond and preferably a compound represented by Chemical Formula 3.

[Chemical Formula 3]

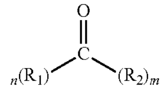

In Chemical Formula 3, $R_1$ and $R_2$ are the same or different, and are each independently an alkyl group having 1 to 10 carbon atoms substituted or unsubstituted by at least one substituent group selected from the group consisting of a hydroxy group, an alkyl group having 1 to 10 carbon atoms, an alkoxy group having 1 to 10 carbon atoms, an alkenyl group having 2 to 10 carbon atoms, an aryl group having 6 to 20 carbon atoms, a cycloalkyl group having 3 to 10 carbon atoms, a heterocyclic group having 2 to 10 carbon atoms, a carbonyl group having 1 to 10 carbon atoms, and a carboalkoxy group having 1 to 10 carbon atoms; an alkenyl group having 2 to 10 carbon atoms substituted or unsubstituted by at least one substituent group selected from the group consisting of a hydroxy group, an alkyl group having 1 to 10 carbon atoms, an alkoxy group having 1 to 10 carbon atoms, an aryl group having 6 to 20 carbon atoms, a cycloalkyl group having 3 to 10 carbon atoms, a heterocyclic group having 2 to 10 carbon atoms, a carbonyl group having 1 to 10 carbon atoms, and a carboalkoxy group having 1 to 10 carbon atoms; an aryl group having 6 to 20 carbon atoms substituted or unsubstituted by at least one substituent group selected from the group consisting of a halogen group, a hydroxy group, an alkyl group having 1 to 10 carbon atoms, an alkenyl group having 2 to 10 carbon atoms, and an alkoxy group having 1 to 10 carbon atoms; a heterocyclic group having 2 to 20 carbon atoms, which has at least one heteroatom selected from the group consisting of N, O, and S groups and which is substituted or unsubstituted by at least one substituent group selected from the group consisting of an alkyl group having 1 to 10 carbon atoms and an alkoxy group having 1 to 10 carbon atoms; hydrogen; a halogen group; or a hydroxy group, $R_1$ and $R_2$ may be connected to each other to form a ring, and n and m are each independently an integer of 0 to 5.

In Chemical Formula 3, the alkyl group among $R_1$ and $R_2$ may be a straight chain or branched chain, may have 1 to 10 carbon atoms, and may be substituted or unsubstituted by at least one substituent group selected from the group consisting of a hydroxy group, an alkyl group having 1 to 10 carbon atoms, an alkoxy group having 1 to 10 carbon atoms, an alkenyl group having 2 to 10 carbon atoms, an aryl group having 6 to 20 carbon atoms, a cycloalkyl group having 3 to 10 carbon atoms, a heterocyclic group having 2 to 10 carbon atoms, a carbonyl group having 1 to 10 carbon atoms, and a carboalkoxy group having 1 to 10 carbon atoms. Specific examples of the alkyl group may include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methyl-hexyl, and ethyl propionate groups, but are not limited thereto.

Further, in Chemical Formula 3, the alkenyl group among $R_1$ and $R_2$ may be a straight chain or branched chain, may preferably have 2 to 10 carbon atoms, and may be substituted or unsubstituted by at least one substituent group selected from the group consisting of a hydroxy group, an alkyl group having 1 to 10 carbon atoms, an alkoxy group having 1 to 10 carbon atoms, an aryl group having 6 to 20 carbon atoms, a cycloalkyl group having 3 to 10 carbon atoms, a heterocyclic group having 2 to 10 carbon atoms, a carbonyl group having 1 to 10 carbon atoms, and a carboalkoxy group having 1 to 10 carbon atoms. Specific examples of the alkenyl group may include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl) vinyl-1-yl, 2,2-bis(diphenyl-1-yl) vinyl-1-yl, a stilbenyl group, a styrenyl group, and 2,6-dimethylhepta-1,5-diene, but are not limited thereto.

Further, in Chemical Formula 3, the aryl group among $R_1$ and $R_2$ may be a monocyclic aryl group or a polycyclic aryl group. When the aryl group is the monocyclic aryl group, the aryl group may preferably have 6 to 20 carbon atoms and may be substituted or unsubstituted by at least one substituent group selected from the group consisting of a halogen group, a hydroxy group, an alkyl group having 1 to 10 carbon atoms, an alkenyl group having 2 to 10 carbon atoms, and an alkoxy group having 1 to 10 carbon atoms. Specific examples of the monocyclic aryl group may include a phenyl group, a biphenyl group, a terphenyl group, a styrene group, a 1-chlorophenyl group, and a 2-methoxyphenol group, but are not limited thereto. Specific examples of the polycyclic aryl group may include a naphthyl group, an anthracenyl group, a phenanthryl group, a pyrenyl group, a perylenyl group, a chrysenyl group, and a fluorenyl group, but are not limited thereto.

Further, in Chemical Formula 3, the heterocyclic group among $R_1$ and $R_2$ is a heterogeneous element and an aromatic or aliphatic heterocyclic group containing at least one of 0, N, and S. The number of carbon atoms thereof is not particularly limited, but preferably 2 to 10. The heterocyclic group may be substituted or unsubstituted by at least one substituent group selected from the group consisting of an alkyl group having 1 to 10 carbon atoms and an alkoxy group having 1 to 10 carbon atoms. Examples of the heterocyclic group may include a thiophene group, a furan group, a pyrrole group, an imidazole group, a thiazole group, an oxazole group, an oxadiazole group, a triazole group, a pyridine group, a bipyridine group, a pyrimidine group, a triazine group, a triazole group, an acridine group, a pyridazine group, a pyrazine group, a quinoline group, a quinazoline group, a quinoxaline group, a phthalazine group, a pyrido pyrimidinyl group, a pyrido pyrazinyl group, a pyrazino pyrazinyl group, an isoquinoline group, an indole group, a carbazole group, a carboline group, a benzoxazole group, a benzoimidazole group, a benzothiazole group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group, a dibenzofuranyl group, a 2-methylfuran group, and a furan group substituted by methanol, but are not limited thereto.

Further, in Chemical Formula 3, the halogen group among $R_1$ and $R_2$ is F—, Cl—, Br—, or I—, and at least one of F—, Cl—, and Br— may be preferably selected.

For example, the substrate may be at least one selected from among furfural, levulinic acid, 5-hydroxymethylfurfural (HMF), glycerol, fructose, glucose, 5-methyl furfural, butyl levulinate (BL), 1-(hydroxyethyl)benzene (1-HB), 7-keto-LCA (7-ketone-lithocholic acid), vanillin, citral, cinnamic aldehyde, carvone, ethyl levulinate, benzaldehyde, 4-chlorobenzaldehyde, acetophenone, and levulinic acid (LA).

Further, the hydrogen donor may be isopropanol, methanol, ethanol, glycerol, butanol, benzyl alcohol, cyclohexanol, 2-propanol, ethylene glycol, glucose, xylose, fructose, sorbitol, mannose, galactose, mannitol, galactitol, xylitol, glycerol, or a mixture thereof.

Further, the hydrogen donor may be petroleum-based alcohol or biomass-based alcohol.

A modified metal-organic framework of the present disclosure significantly improves the efficiency of the catalytic hydrogenation reaction through modification of a metal node and a local structure.

Further, since catalytic activity is exhibited even at temperatures close to room temperature, process efficiency is ensured, and low-grade waste heat is capable of being used in the production of chemical materials derived from biomass, which is environmentally friendly.

DESCRIPTION OF THE PREFERRED EMBODIMENTS

Hereinafter, the present disclosure will be described in detail.

The present disclosure provides a modified metal-organic framework obtained by modifying a metal-organic framework using a compound having a hydroxyl group (—OH), and a catalyst for a hydrogenation reaction including the same.

In more detail, in the case of the modified metal-organic framework according to the present disclosure, the metal-organic framework is activated using the compound having the hydroxyl group to modify a local structure thereof. The compound having the hydroxyl group (—OH) is not limited, but alcohol is preferable, and at least one of methanol, ethanol, and propanol may be more preferable.

In an embodiment of the present disclosure, the metal-organic framework may be at least one selected from among MOF-808, PCN-700, PCN-777, PCN-222, PCN-225, NU-902, NU-901, NU-1000, NU-1200, BUT-12, DUT-51, MOF-545, MMPF-6, MOF-841, and hcp UiO-66.

MOF-808 will be described as an example of the modified metal-organic framework according to the present disclosure.

Figure 1:
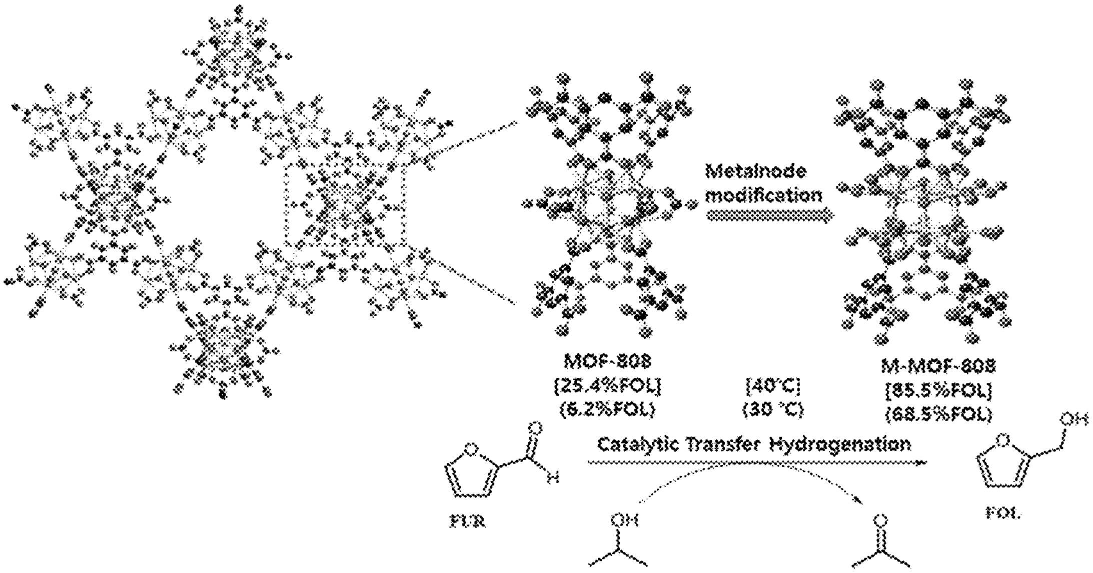
FIG. 1 shows a modified MOF-808 of the present disclosure.

FIG. 1 shows the structures of MOF-808 and modified MOF-808 (MMOF-808) of the present disclosure and a catalytic hydrogenation pathway from FUR to FOL using the same.

The metal node coordination (connectivity) of the MOF-808-based metal-organic framework is 10 or less and preferably 6. The metal is a Group 4A or 4B element or a lanthanide-based metal having an oxidation state of $4^+$, and may be preferably at least one selected from among Zr, Ce, and Hf.

In detail, the modified metal-organic framework is represented by the following Chemical Formula 1 or Chemical Formula 2.

$$M_6O_{4+x}(OH)_m(BTC)_2(OR)_n \quad \text{[Chemical Formula 1]}$$

(M is a Group 4A or 4B element on a periodic table or a lanthanide-based metal having an oxidation state of $4^+$, x is greater than 0, a sum of m and n is 10 or less, m is greater than n, and R is an alkyl group having 1 to 10 carbon atoms)

$$M_6(\mu_3\text{-}O)_4(\mu_3\text{-}OH)_4(OH)_x(H_2O)_6(BTC)_2(OR)_y \quad \text{[Chemical Formula 2]}$$

(x is any number greater than 0 and less than or equal to 12, y is any number from 0 to 6, M is a Group 4A or 4B element or a lanthanide-based metal having an oxidation state of $4^+$, and R is an alkyl group having 1 to 10 carbon atoms)

In Chemical Formulas 1 and 2, the modified metal-organic framework of the present disclosure is modified using the compound having the hydroxyl group, and thus may or may not contain an alkoxy group bonded to metal M (M-OR), and when M-OR is not contained, the alkoxy group is substituted by a hydroxyl group.

An aspect of the present disclosure provides a catalyst for a hydrogenation reaction including the modified metal-organic framework.

The catalyst may perform a hydrogenation reaction in a heterogeneous catalyst system. The substrate capable of performing the hydrogenation reaction is not limited, but may be a compound having a C═O bond, preferably a carbonyl compound, and more preferably a compound represented by Chemical Formula 3.

[Chemical Formula 3]

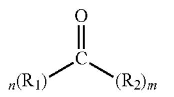

In Chemical Formula 3, $R_1$ and $R_2$ are the same or different, and are each independently an alkyl group having 1 to 10 carbon atoms substituted or unsubstituted by at least one substituent group selected from the group consisting of a hydroxy group, an alkyl group having 1 to 10 carbon atoms, an alkoxy group having 1 to 10 carbon atoms, an alkenyl group having 2 to 10 carbon atoms, an aryl group having 6 to 20 carbon atoms, a cycloalkyl group having 3 to carbon atoms, a heterocyclic group having 2 to 10 carbon atoms, a carbonyl group having 1 to 10 carbon atoms, and a carboalkoxy group having 1 to 10 carbon atoms; an alkenyl group having 2 to 10 carbon atoms substituted or unsubstituted by at least one substituent group selected from the group consisting of a hydroxy group, an alkyl group having 1 to 10 carbon atoms, an alkoxy group having 1 to 10 carbon atoms, an aryl group having 6 to 20 carbon atoms, a cycloalkyl group having 3 to 10 carbon atoms, a heterocyclic group having 2 to 10 carbon atoms, a carbonyl group having 1 to 10 carbon atoms, and a carboalkoxy group having 1 to 10 carbon atoms; an aryl group having 6 to 20 carbon atoms substituted or unsubstituted by at least one substituent group selected from the group consisting of a halogen group, a hydroxy group, an alkyl group having 1 to 10 carbon atoms, an alkenyl group having 2 to 10 carbon atoms, and an alkoxy group having 1 to 10 carbon atoms; a heterocyclic group having 2 to 20 carbon atoms, which has at least one heteroatom selected from the group consisting of N, O, and S groups and which is substituted or unsubstituted by at least one substituent group selected from the group consisting of an alkyl group having 1 to 10 carbon atoms and an alkoxy group having 1 to 10 carbon atoms; hydrogen; a halogen group; or a hydroxy group, $R_1$ and $R_2$ may be connected to each other to form a ring, and n and m are each independently an integer of 0 to 5.

In Chemical Formula 3, the alkyl group among $R_1$ and $R_2$ substituent groups may be a straight chain or branched chain, may have 1 to 10 carbon atoms, and may be substituted or unsubstituted by at least one substituent group selected from the group consisting of a hydroxy group, an alkyl group having 1 to 10 carbon atoms, an alkoxy group having 1 to 10 carbon atoms, an alkenyl group having 2 to 10 carbon atoms, an aryl group having 6 to 20 carbon atoms, a cycloalkyl group having 3 to 10 carbon atoms, a heterocyclic group having 2 to 10 carbon atoms, a carbonyl group having 1 to 10 carbon atoms, and a carboalkoxy group having 1 to 10 carbon atoms. Specific examples of the alkyl group may include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and ethyl propionate groups, but are not limited thereto.

Further, in Chemical Formula 3, the alkenyl group may be a straight chain or branched chain, may preferably have 2 to 10 carbon atoms, and may be substituted or unsubstituted by at least one substituent group selected from the group consisting of a hydroxy group, an alkyl group having 1 to 10 carbon atoms, an alkoxy group having 1 to 10 carbon atoms, an aryl group having 6 to 20 carbon atoms, a cycloalkyl group having 3 to 10 carbon atoms, a heterocyclic group having 2 to 10 carbon atoms, a carbonyl group having 1 to 10 carbon atoms, and a carboalkoxy group having 1 to 10 carbon atoms. Specific examples of the alkenyl group may include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl) vinyl-1-yl, 2,2-bis(diphenyl-1-yl) vinyl-1-yl, a stilbenyl group, a styrenyl group, and 2,6-dimethylhepta-1,5-diene, but are not limited thereto.

Further, in Chemical Formula 3, the aryl group may be a monocyclic aryl group or a polycyclic aryl group. When the aryl group is the monocyclic aryl group, the aryl group may preferably have 6 to 20 carbon atoms and may be substituted or unsubstituted by at least one substituent group selected from the group consisting of a halogen group, a hydroxy group, an alkyl group having 1 to 10 carbon atoms, an alkenyl group having 2 to 10 carbon atoms, and an alkoxy group having 1 to 10 carbon atoms. Specific examples of the monocyclic aryl group may include a phenyl group, a biphenyl group, a terphenyl group, a styrene group, a 1-chlorophenyl group, and a 2-methoxyphenol group, but are not limited thereto. Specific examples of the polycyclic aryl group may include a naphthyl group, an anthracenyl group, a phenanthryl group, a pyrenyl group, a perylenyl group, a chrysenyl group, and a fluorenyl group, but are not limited thereto.

Further, in Chemical Formula 3, the heterocyclic group is a heterogeneous element and an aromatic or aliphatic heterocyclic group containing at least one of 0, N, and S. The number of carbon atoms thereof is not particularly limited, but preferably 2 to 10. The heterocyclic group may be substituted or unsubstituted by at least one substituent group selected from the group consisting of an alkyl group having 1 to 10 carbon atoms and an alkoxy group having 1 to 10 carbon atoms. Examples of the heterocyclic group may include a thiophene group, a furan group, a pyrrole group, an imidazole group, a thiazole group, an oxazole group, an oxadiazole group, a triazole group, a pyridine group, a bipyridine group, a pyrimidine group, a triazine group, a triazole group, an acridine group, a pyridazine group, a pyrazine group, a quinoline group, a quinazoline group, a quinoxaline group, a phthalazine group, a pyrido pyrimidinyl group, a pyrido pyrazinyl group, a pyrazino pyrazinyl group, an isoquinoline group, an indole group, a carbazole group, a carboline group, a benzoxazole group, a benzoimidazole group, a benzothiazole group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group, a dibenzofuranyl group, a 2-methylfuran group, and a furan group substituted by methanol, but are not limited thereto.

Further, in Chemical Formula 3, the halogen group is F—, Cl—, Br—, or I—, and at least one of F—, Cl—, and Br— may be preferably selected.

For example, the substrate may be at least one selected from among furfural, levulinic acid, 5-hydroxymethylfurfural (HMF), glycerol, fructose, glucose, 5-methyl furfural, butyl levulinate (BL), 1-(hydroxyethyl)benzene (1-HB), 7-keto-LCA (7-ketone-lithocholic acid), vanillin, citral, cinnamic aldehyde, carvone, ethyl levulinate, benzaldehyde, 4-chlorobenzaldehyde, acetophenone, and levulinic acid (LA).

Examples of the hydrogenation reaction using the substrate may include a hydrogenation reaction of furfural to furfuryl alcohol, a hydrogenation reaction of levulinic acid (LA) to gamma-valerolactone (GVL), a hydrogenation reaction of furfural to 2-methylfuran (2-MF), a hydrogenation reaction of 5-hydroxymethylfurfural (HMF) to 2,5-dimethylfuran (DMF), a hydrogenation reaction of glycerol to 1,2-propanediol (1,2-PDO), a hydrogenation reaction of fructose to 5-hydroxymethylfurfural, a hydrogenation reaction of glucose to gamma-valerolactone, a hydrogenation reaction of fructose to gamma-valerolactone, a hydrogenation reaction of butyl levulinate (BL) to gamma-valerolactone, a hydrogenation reaction of glycerol to 1,2-PDO, a hydrogenation reaction of 1-(hydroxyethyl)benzene (1-HB) to ethylbenzene, a hydrogenation reaction of 5-hydroxymethylfurfural to 1,6-hexanediol (HDL), a hydrogenation reaction of 7-keto-LCA (7-ketone-lithocholic acid), which is a pharmaceutical intermediate, to UDCA (ursodeoxycholic acid), a hydrogenation reaction of vanillin to vanilly alcohol, a hydrogenation reaction of citral to nerol and/or geraniol, a hydrogenation reaction of cinnamic aldehyde to cinnamyl alcohol, and a hydrogenation reaction of carvone to carveol, but are not limited thereto.

Further, a material that may be used as a hydrogen donor in the hydrogenation reaction is a material having a-OH group in the structure of a compound, and petroleum-based alcohols or biomass-based alcohols and chain or cyclic alcohols are capable of being used. Examples of these materials that are usable may include, but are not limited to, isopropanol, methanol, ethanol, glycerol, butanol, benzyl alcohol, cyclohexanol, 2-propanol, ethylene glycol, glucose, xylose, fructose, sorbitol, mannose, galactose, mannitol, galactitol, xylitol, glycerol, or a mixture thereof.

Further, the hydrogenation reaction may be performed at a temperature of 150° C. or lower using the modified metal-organic framework catalyst according to the present disclosure. In particular, the modified metal-organic framework exhibits the efficiency of hydrogenation reaction even at a low temperature of 30 to 40° C., thus being applicable as a catalyst even to biomass-derived materials.

Further, the hydrogenation reaction catalyst according to the present disclosure exhibits efficiency with respect to the hydrogenation reaction even when continuously reused.

Further, the present disclosure provides a method of manufacturing the catalyst for the hydrogenation reaction.

The method of manufacturing the catalyst includes immersing a metal-organic framework in a compound having a hydroxyl group to manufacture a mixture, performing refluxing while heating the mixture to or above a boiling point of the compound having the hydroxyl group, and filtering, washing, and drying the metal-organic framework after the refluxing. The compound having the hydroxyl group may be at least one selected from among methanol, ethanol, and propanol.

Further, the present disclosure provides a method of producing a reduced organic compound, which includes performing a hydrogenation reaction between an organic compound substrate and a hydrogen donor using the catalyst according to the present disclosure.

The organic compound substrate may be a compound having a C═O bond, preferably a carbonyl compound, and more preferably a compound represented by Chemical Formula 3.

In the method of producing the organic compound, the hydrogen donor may be petroleum-based and biomass-based alcohol.

Hereinafter, the present disclosure will be described in more detail with reference to preferred Examples. However, it will be apparent to those of ordinary skill in the art that these Examples are intended to describe the present disclosure in more detail and the scope of the present disclosure is not limited thereto.

[Chemical Medicines and Materials]

Among the reagents used in this Example, furfural (FUR, 99%), furfuryl alcohol (FOL, 98%), methanol (MeOH, 99.8%), ethanol (EtOH, 99.8%), 1-propanol (1-PrOH, 99.7%), 2-butanol (2-BuOH, 99.5%), cyclopentanol (C-PeOH, 99%), isopropyl alcohol (IPA/2-PrOH, 99.5%), naphthalene (99%), tert-butanol (99.5%), methanol-d4 (99.8%), 2-propanol-d8 (99.5%), 5-(hydroxymethyl) furfural (5-HMF, 99%), ethyl levulinate (99%), 5-methylfurfural (99%), benzaldehyde (99%), 4-chlorobenzaldehyde (97%), acetophenone (99%), $ZrOCl_2 \cdot 8H_2O$ (99.5%), $ZrCl_4$ (99.9%), 1,4-benzenedicarboxylic acid (BDC, 98%), biphenyl-4,4'-dicarboxylic acid (BPDC, 97%), 1,3,5-benzenetricarboxylic acid (BTC, 95%), 2,5-thiophenedicarboxylic acid (TDC, 99%), hydrochloric acid (HCl, 37%), and an ammonium hydroxide solution (30%-33%) were purchased from Sigma-Aldrich to use. As N, N-dimethylformamide (DMF, 99.5%), benzoic acid (99.5%), formic acid (99%), and acetic acid (99.7%), products manufactured by Samchun Pure Chemicals (Korea) were used. 2,6-naphthalene dicarboxylic acid (NDC, 98%) was obtained from Alfa Aesar. All of the above chemical materials were used without further purification.

Preparation Example

Synthesis of Scaled-Up MOF-808

$ZrOCl_2 \cdot 8H_2O$ (13.5 g, 0.04 mol) and 1,3,5-benzenetricarboxylic acid (9.3 g, 0.04 mol) were dissolved in a mixed solution of DMF/formic acid (164 ml/160 ml) to prepare a reaction mixture. The reaction mixture was agitated at room temperature and then heated in a 700 ml Teflon-lined pressure reactor at 135° C. for 48 hours to complete the reaction, and the resultant mixture was cooled to room temperature. Next, after filtering was performed to obtain a powder, the powder was washed twice with DMF (1 L) to remove unreacted ligand molecules from the pores of MOF-808, and then washed twice using acetone (1 L). This process of removing the DMF filling the pores of MOF-808 was performed for 2 days, and the obtained solid powder was dried in an oven at 100° C. overnight.

Synthesis of M-MOF-808 (Modified MOF-808)

The prepared MOF-808 (1 g) was immersed in 100 ml of anhydrous methanol contained in a 250 ml round bottom flask, and then refluxed for 8 hours at the boiling point of methanol. Thereafter, the powder was filtered and washed twice with 150 ml of fresh methanol at room temperature for 24 hours. Next, the obtained sample was dried in a vacuum oven at 80° C. for 12 hours. The MOF-808 powder treated with methanol was designated as M-MOF-808.

Synthesis of E-MOF-808 and P-MOF-808

E-MOF-808 (immersion in ethanol) and P-MOF-808 (immersion in propanol) were obtained in the same manner as the synthesis method of M-MOF-808, except that MOF-808 was immersed in ethanol or 1-propanol.

Synthesis of UiO-66 (Zr)

UiO-66 (Zr) was synthesized in a 500 ml two-neck round bottom flask (RBF). $ZrOCl_2 \cdot 8H_2O$ (5.7 g, 0.018 mol) as a zirconium precursor was dissolved in a solution of DMF (282 mL, 36.3 mol) and benzoic acid (32.4 g, 2.6 mol). 1,4-benzene dicarboxylic acid (3.9 g, 0.023 mol) as a linker was added to a clear solution of the zirconium precursor and agitated at room temperature for 20 minutes, and 37% (2.1 mL) hydrochloric acid was added to the solution.

Subsequently, the RBF containing the solution was heated in an oil bath at 120° C. for 24 hours. Then, the solution was cooled to room temperature, the precipitate was and separated using filtration. The obtained solid was washed twice with DMF (500 ml) for 24 hours. The generated particles were washed with ethanol (500 mL) in the same manner as DMF. Finally, the solid was dried in an oven at 100° C. overnight.

Synthesis of UiO-67

The synthesis procedure of UiO-67 was performed with a 20-fold magnification of the method reported by Salomon et al. (Chem. Commun. 2015, 51, 2972-2975). $ZrCl_4$ (2.32 g, 10 mmol), biphenyl-4,4'-dicarboxylic acid (2.5 g, 10 mmol), and benzoic acid (36.7 g, 300 mmol) were dissolved in 200 mL of DMF filling a 1 L Teflon-lined autoclave, and 1.64 ml of 37% hydrochloric acid was added thereto. All reactants were agitated before heating. The mixture was heated at 120° C. for 24 hours and cooled to room temperature after completion of the reaction. Thereafter, the solid was filtered, washed twice with DMF (500 mL) and acetone (500 mL) for 30 hours, and dried in an oven at 100° C. overnight to obtain UiO-67.

Synthesis of DUT-52

DUT-52 was synthesized by slightly modifying the method reported in a document (CrystEngComm 2013, 15, 9572-9577). After $ZrCl_4$ (0.46 g, 2.0 mmol) and 2,6-naphthalene dicarboxylic acid (0.44 g, 2.0 mmol) were dissolved in 40 mL of DMF, acetic acid (6 mL, 100 mmol) was introduced into the solution and agitated at room temperature for several minutes. The generated solution was transferred to a 100 mL Teflon-lined pressure autoclave and heated at 120° C. for 24 hours. The obtained solid was collected using filtration and washed three times with fresh DMF (500 mL), and then DMF was washed twice with ethanol (500 mL). Thereafter, the obtained compound was dried in a vacuum oven at 120° C. for 12 hours to obtain DUT-52.

Synthesis of DUT-67

$ZrOCl_2 \cdot 8H_2O$ (3.8 g, 11.8 mmol) and 2,5-thiophenedicarboxylic acid (1.4 g, 8 mmol) in a solvent mixture of DMF/formic acid (200 mL/111 mL) were placed into a 700 mL Teflon-lined autoclave and then heated at 135° C. for 48 hours. The white powder obtained was collected and washed three times with DMF and then three times with acetone for 48 hours. The obtained solid was dried in an oven at 100° C. overnight to obtain DUT-67.

Synthesis of $ZrO(OH)_2$ and $ZrO_2$

Zirconium oxide was synthesized according to a document (Appl. Catal. B Environ. 2014, 147, 827-834). Concentrated $NH_4OH$ was added to an aqueous solution of $ZrOCl_2 \cdot 8H_2O$ (100 $gL^{-1}$), and the pH of the solution was adjusted to 9 to 10 with vigorous agitation. The generated emulsion was aged for 24 hours, filtered, and washed thoroughly with water. The obtained solid precipitate was dried at 100° C. overnight to obtain $ZrO(OH)_2$. The obtained $ZrO(OH)_2$ was calcined in air at 500° C. for 5 hours to prepare $ZrO_2$.

<Catalyst Analysis>

PXRD (powder diffraction patterns) was obtained using a Rigaku diffractometer with Ni-filtered Cu-Kα-radiation (40 kV, 30 mA, λ=1.5406 Å).

The $N_2$ adsorption-desorption isotherm was obtained at −196° C. using Micromeritics Tristar 3000, and samples were dehydrated in a vacuum at 150° C. for 12 hours before analysis.

The pore size distribution was calculated using a density function theory (DFT).

In the case of ultra-microporous MOF (UiO-66 and DUT-52), samples were pretreated at 150° C. for 12 hours in a vacuum before Ar adsorption, and then Ar adsorption isotherms were obtained at −186° C. using Micromeritics ASAP 2020.

The specific surface area was evaluated using a BET method, and the pore volume was determined using a single-point method at $p/p^0$ of 0.99. The ultrafine pore size distribution was measured using a Horvath-Kawazoe method.

Thermogravimetric analysis (TGA) of the catalyst was performed using a Scinco TGA-N 1000 thermal analyzer while the samples were heated at a heating rate of 5° C. min-1 at 25 to 700° C. under a constant air flow of 30 ml min-1.

The morphological properties of the catalyst were observed using a scanning electron microscope (SEM) and a transmission electron microscope (TEM).

Before the adsorption step, the samples were activated in a helium flow at 150° C. for 12 hours, the activated samples were exposed to $NH_3$ or $CO_2$ gas at 50° C. for 30 minutes at a flow rate of 50 mL/min, the $NH_3$ or $CO_2$ gas that was physically adsorbed was removed by purging with helium gas for 1 hour at the same temperature and flow rate, and then the TPD profile of the catalyst was measured. TPD data were measured using a Micromeritics AutoChem II 2920 V3.05 device equipped with a TCD between 50° C. and 400° C. at 5° C./min.

The content of Zr in liquid (a reaction solution for determining the leaching of Zr from the MOF structure) and solid (MOF powder) was determined using inductively coupled plasma (ICP) analysis.

Elemental analysis was performed to determine the carbon and hydrogen contents in the catalyst.

The 1H NMR spectrum of the digested MOF sample was measured at 500 MHZ. After 10 mg of MOF digested in a solution of 20 μL of HF and 580 μL of DMSO-d6 was agitated for 5 minutes, $^1$H NMR was performed with a clear digested solution.

After the samples were palletized and evacuation was performed in a vacuum (<$3.0\times10^{-6}$ torr) at 30 to 400° C. for 2 hours, the IR spectrum was obtained at room temperature using a Nicolet is-50 spectrometer having an in-situ IR cell with a KBr window.

<CO-FTIR>

The coordinativedly unsaturated sites (CUS) of the metal in the metal-organic framework were measured by FT-IR of adsorbed CO using a Nicolet is-50 device equipped with a mercury cadmium telluride detector. Each sample was prepared as a self-supporting wafer (approximately 10 mg/cm$^2$) and disposed in a quartz cell equipped with a $CaF_2$ window. The pellets were adjusted with a quartz sample holder movable in infrared beams for spectrum acquisition, and displacement from the top of the cell to the furnace was performed for heat treatment. The cell was connected to a vacuum line for the steps of introducing CO into the IR cell and performing evacuating and calcining. Before CO adsorption, the sample was activated in the IR cell at 150° C. under a condition of less than $3.0\times10^{-6}$ torr for 6 hours.

In the CO adsorption experiment, after thermal activation, the sample holder was cooled with liquid nitrogen to reduce the temperature of the pellet to about-173° C. Incremental addition of CO probe molecules in the cell was performed using a calibrated volume (3.99 cm$^3$) connected to a pressure gauge for controlling a probe pressure (0.01 to 2.0 torr).

<Catalyst Experiment and Result Analysis>

The catalytic activity of Zr-MOF in the hydrogenation reaction of furfural was evaluated using various alcohols as a hydrogen donor material. Zr-MOF was dried in an oven at 100° C. for 12 hours before used. In a typical procedure, known amounts of the dried catalyst, furfural, naphthalene, and proton donor/solvent as internal standards were placed in a two-neck round bottom flask (RBF). After the reaction mixture of the RBF equipped with a rubber diaphragm and a reflux condenser was heated at the desired temperature for the required time, the catalyst was separated using centrifugation, followed by thorough washing with hot methanol and drying at 100° C. before a subsequent cycle.

Freshly distilled furfural neutralized in $Na_2CO_3$ was only used in recycling tests for minimizing the colored and acidic impurities present therein. The filtrate collected after the reaction was quantitatively analyzed using gas chromatography (GC, FID detector and HP-5 column), and the product was confirmed using GC-MS (Agilent 6890 N GC and 5973 N MSD). The conversion rate of furfural and the yield of furfuryl alcohol were determined using a multiple-point internal standard calibration method.

Different carbonyl substrates and hydrogenated products thereof were quantitatively analyzed using a single-point internal standard calibration method. In gas analysis, a GC equipped with an FID detector and a DB-624 column was used.

Analysis of Catalytic Activity According to Metal Node Connectivity

In the hydrogenation reaction from FUR to FOL, in order to investigate the effect of metal node connectivity and porosity on the catalytic activity of Zr-MOFs, Zr-MOFs having different metal node coordinations (connectivities) of 12, 8, and 6 and different porosities were synthesized. With respect thereto, the experiment of the hydrogenation reaction from FUR to FOL was conducted at 82° C., and textural properties were analyzed and are shown in the following Table 1. In Table 1, CN means the coordination number of the metal node to a connective group, and TOF (turnover frequency) was calculated by (moles of FOL)/(moles of "Zr" from ICP analysis×time) at a reaction time of 2 h.

Figure 2:
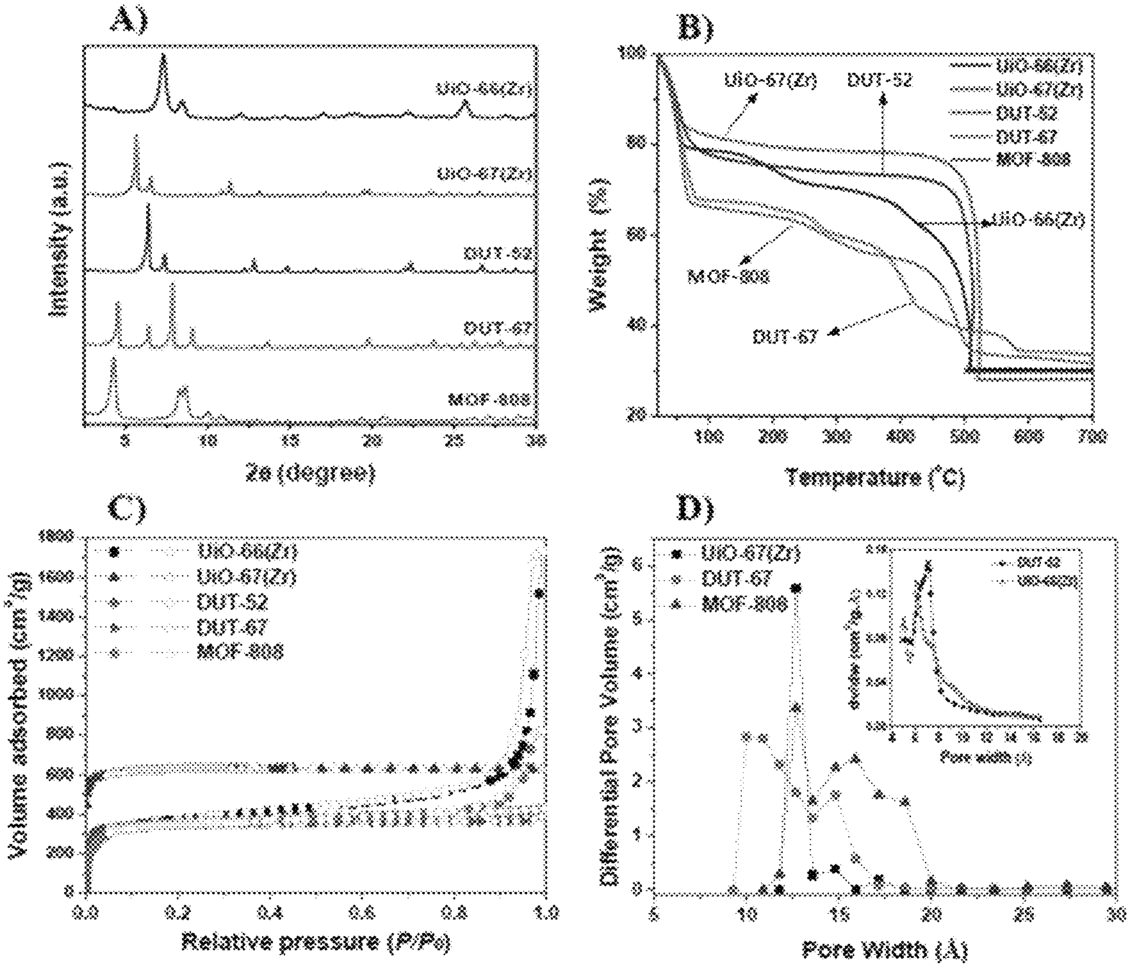
FIG. 2 shows the results of PXRD, TGA, and $N_2$-physical adsorption analyses of synthesized Zr-MOFs.

The synthesized Zr-MOFs were analyzed using PXRD, TGA, and $N_2$-physical adsorption, and the results are shown in FIG. 2.

FIG. 2A shows the result of PXRD, FIG. 2B shows the result of TGA analysis, FIG. 2C shows the result of $N_2$ adsorption-desorption of Zr-MOFs at −196° C., and FIG. 2D shows the pore size distributions calculated using a DFT method for UiO-67, DUT-67, and MOF-808 and using a HK method for UiO-66 and DUT-52.

According to FIG. 2A, formation of a crystalline phase is confirmed in all Zr-MOFs. Although the crystallinity of MOF-808 is lower than that of the original structure reported in advance, it is believed that this is because the Zr-MOFs were prepared through scale-up synthesis for achieving a higher batch yield. According to result of the TGA analysis of FIG. 2B, it is shown that all of the synthesized Zr-MOFs are thermally stable enough to perform hydrogenation reactions at an appropriate reaction temperature.

Further, as confirmed in FIGS. 2C and 2D, all of the synthesized Zr-MOFs include very well-developed pores and have a well-defined pore size.

The tissue properties and catalytic activity of various Zr-MOFs used for hydrogenation of FUR are summarized in Table 1.

In the table below, SBET refers to the surface area by a BET method, PD refers to the pore diameter, AS refers to the amount of acid determined by $NH_3$-TPD, and BS refers to the amount of base determined by $CO_2$-TPD. $Y_{FOL}$ refers to the yield of furfuryl alcohol, $S_{FOL}$ refers to the selectivity of furfuryl alcohol, and CN refers to the coordination number of the metal node to the linker.

The turnover frequency (TOF) was calculated by (moles of FOL)/(moles of "Zr" from ICP analysis×time) at a reaction time of 2 h.

With respect to the reaction condition in Table 2, 1 g (10.4 mmol) of FUR, 25 g (416 mmol) of IPA, and 0.1 g of the catalyst were mixed, refluxing was performed at a temperature of 82° C., and the reaction was performed for 2 hours to obtain the reaction result.

TABLE 1

| No. | Zr-MOF (CN) | BET surface BET area (m2/g) | Pore diameter (Å) | Acid site (mmol/g) | Base site (mmol/g) | Conversion rate (%) | FOL yield (%) | FOL selectivity (%) | TOF (h$^{-1}$) | Zr content by ICP (%) | Zr mol % in 0.1 g of catalyst |
|---|---|---|---|---|---|---|---|---|---|---|---|
| 1 | — | | | | | <2.0 | 0 | 0 | | | |
| 2 | UiO-66 (12) | 1210 | 5, 6.1 | 0.35 | 0.05 | 2.3 | 1.3 | 56.5 | 0.26 | 24.4 | 2.6 |
| 3 | DUT-52 (12) | 1208 | 7.1 | 0.65 | 0.06 | 2.1 | 0.0 | 0.0 | 0.0 | 22.2 | 2.3 |
| 4 | UiO-67 (12) | 2518 | 12.7 | 0.60 | 0.04 | 5.2 | 0.1 | 1.9 | 0.02 | 24.8 | 2.6 |
| 5 | DUT-67 (8) | 1362 | 10, 4.9 | 0.74 | 0.10 | 16.4 | 13.5 | 82.3 | 2.0 | 32.3 | 3.4 |
| 6 | MOF-808 (6) | 1313 | 12.7, 15.9 | 0.85 | 0.15 | 81.3 | 66.4 | 81.7 | 11.6 | 27.3 | 3.0 |

All of the Zr-MOFs in Table 1 have high porosity, and pore diameters thereof are well defined. No. 1 in Table 1 is the result of the hydrogenation reaction of FUR at 82° C. without a catalyst, showing that no FOL was generated even after the reaction for 2 hours and the FUR conversion rate was less than 2%.

Through the comparison of UiO-66, UiO-67, and DUT-52 having the same ligand as the metal node coordination (12), Table 1 shows that the conversion rate of UiO-67 is only increased by about 3% even though UiO-67 has a higher specific surface area and larger pores compared to UiO-66 and DUT-52. Accordingly, it can be seen that the improved pore size and surface area do not play an important role in improving the catalytic activity and that 12-connected Zr-MOFs (12 carboxylate ligands connected to metal sites) have low activity in the hydrogenation reaction at 82° C.

On the other hand, DUT-67 (8), which has a metal node coordination number of 8, exhibits an improved conversion rate of 16.4%, even though the specific surface area and pores thereof are smaller than those of UiO-67. Therefore, it can be seen that reducing the metal node connection improves the catalytic activity.

Conclusionally, in the case of MOF-808 (6) having a metal node coordination number of 6, the FUR conversion rate is 81.3%, which is significantly improved compared to that of UiO-67. Further, the results of TOF per Zr content measured by ICP in order to exclude the influence of the Zr content in the catalyst that is used are shown in Table 1. This TOF value shows that MOF-808 (6) has a significantly improved value compared to the other Zr-MOFs in Table 1, demonstrating that the metal node connectivity plays an important role in the hydrogenation reaction from FUR to FOL. In detail, as the metal node coordination number increased, the metal Zr sites are saturated with ligands, making the substrate difficult to access. In contrast, as the metal node connectivity is reduced, the concentration around the metal node is reduced, and thus the accessibility of the substrate molecule to the Zr site is improved, and as a result, high catalytic activity may be exhibited.

Further, it have been reported that acid and base sites in some Zr-based catalysts are active sites and have a significant effect on catalyst performance in transfer hydrogenation reactions.

Figure 3:
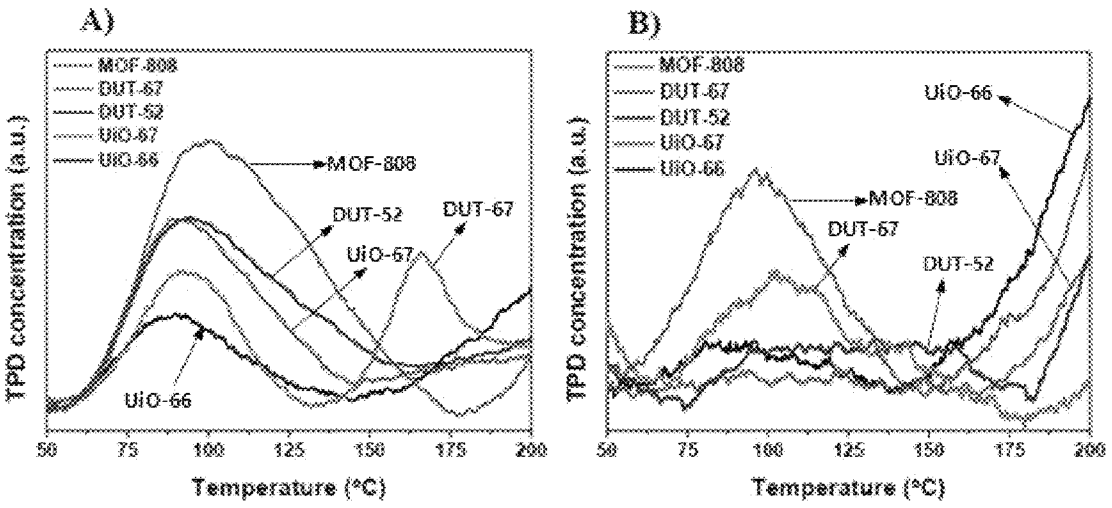
FIG. 3 shows the results of $NH_3$-TPD and $CO_2$-TPD analyses of synthesized Zr-MOFs.

Therefore, NH$_3$-TPD and CO$_2$-TPD analyses were performed to determine the acid-base properties of the catalyst, and the results are shown as A (NH$_3$-TPD) and B(CO$_2$-TPD) in Table 1 and FIG. 3. The reason why the desorption temperature is kept low in the TPD experiment is because the thermal stability of the Zr-MOFs is relatively low.

Although all of the analyzed Zr-MOFs are stable up to 350° C., as demonstrated from the TGA pattern in FIG. 2B, the μ$_3$-OH and formate group of the modulator connected to the Zr node for the purpose of charge balance are disconnected when heated to 200° C. or higher. In the Zr-MOFs, the acid-base sites are caused by a surface hydroxyl group (Zr—OH, base site), μ$_3$-OH (acid site), Zr—OH$_2$ (acid site), framework oxygen Zr—O—C or Zr—O—Zr (base site), and a coordinativedly unsaturated zirconium site (Zr-CUS; acid site) of a metal node.

In the result of NH$_3$-TPD, the increase of the amount of NH$_3$ and the desorption temperature in Zr-MOFs having the coordination reduced cluster indicates that the concentration and intensity of the acid site are increased as the cluster coordination is reduced. This is presumed to be due to the difference in electron density around the cluster caused by the change of the charge of the zirconium node.

The NH$_3$-TPD profile of DUT-67 shows two desorption peaks due to the interaction of ammonia molecules with metal nodes and sulfur-containing thiophene ligands. Since all other Zr-MOFs do not have heteroatoms in the ligand ring structure thereof, only one broad desorption peak as a result of the interaction of NH$_3$ and the metal nodes is shown.

In the Zr-MOFs, both acid and base sites are increased as the cluster coordination is reduced. The acid amount and the base amount of MOF-808 having the highest acid and base sites are 0.85 mmol/g and 0.15 mmol/g, respectively, showing the highest activity to the hydrogenation reaction among the tested Zr-MOFs.

Therefore, the cluster coordination number is reduced to improve the accessibility of the substrate to the Zr-MOFs and also improve the acid-base properties, which correspond to two important factors of remarkably improving the catalyst performance for the hydrogenation reaction.

In all of the above experiments, acetal, which is a major by-product, and two aldol condensation products are observed in the GC-MS analysis. In addition, due to the highly reactive aldehyde group of FUR which is susceptible to a condensation reaction, a polymer product (humin) that is not detected and dissolved may be generated as a by-product.

Analysis Results of MOF-808, M-MOF-808, and d-M-MOF-808

In the M-MOF-808 prepared in the Preparation Example, the local structure thereof is changed by modifying the metal node using methanol. The chemical properties thereof are changed through the local structure modification of the MOF-808, and as a result, the catalytic activity is also changed.

Figure 4:
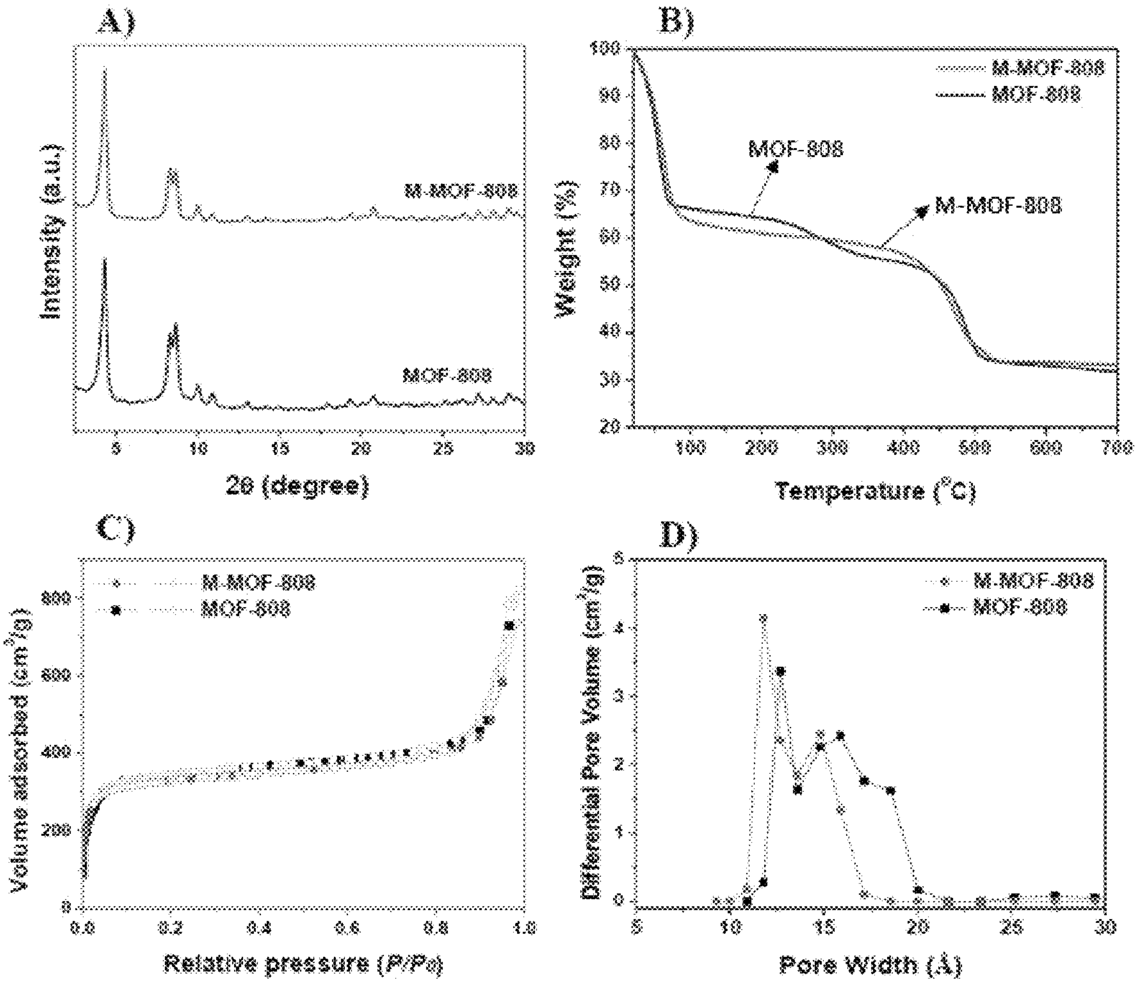
FIG. 4 shows the results of PXRD, TGA, and $N_2$-physical adsorption analyses of MOF-808, M-MOF-808, and d-M-MOF-808.

The results of analysis of the catalyst are shown in FIG. 4. From the PXRD result of FIG. 4A, it can be seen that there is no change in the crystal structure of MOF-808 during the modification process with treatment using methanol. Referring to the TGA analysis result of FIG. 4B, the mass of MOF-808 before the modification is reduced at about 100° C., 225 to 350° C., and 400 to 550° C. The first mass reduction corresponds to the physically absorbed water, the second reduction corresponds to the remaining formate, 113-OH, and trace amounts of DMF, and the third reduction occurs as the MOF is pyrolyzed. However, in the case of the M-MOF-808 modified with methanol, the mass reduction is not observed at 225 to 350° C., which means that the formate, 13-OH, and physically adsorbed DMF were completely removed through the methanol modification.

Figure 5:
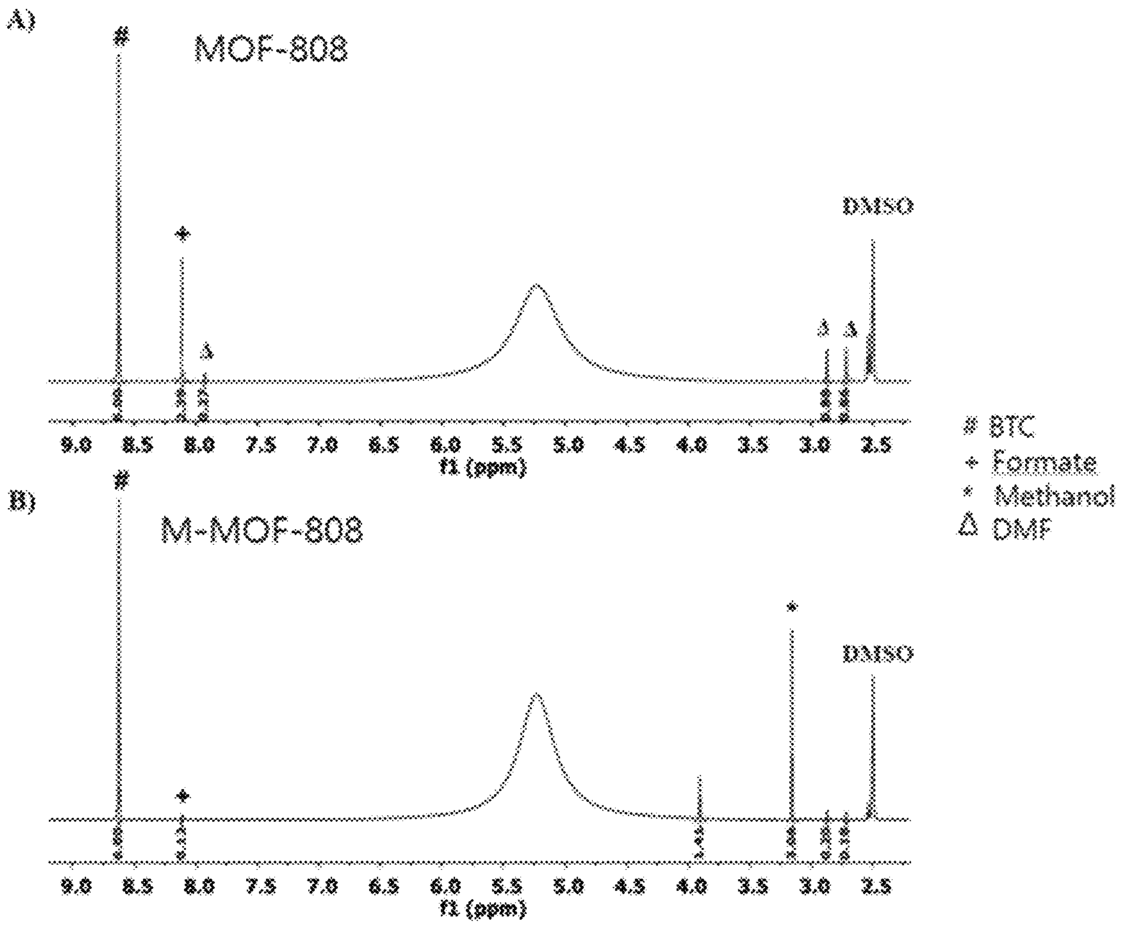
FIG. 5 is $^1H$ NMR spectra of MOF-808 and M-MOF-808.

This is confirmed by 1H NMR spectra of MOF-808 and M-MOF-808 decomposed (digested) in HF/DMSO-d6 (FIG. 5). The results of FIGS. 4C and 4D show that the surface area and pore size of the MOF-808 are slightly reduced but the porosity property thereof is not significantly affected after the methanol activation.

The elemental composition and porosity properties of MOF-808 and M-MOF-808 are summarized in the following Table 2.

TABLE 2

| MOF | BET surface area (m2/g) | Pore diameter (Å) | Acid site (mmol/g) | Base site (mmol/g) | Zr (% ) | C (%) | H (%) |
|---|---|---|---|---|---|---|---|
| MOF-808 | 1313 | 12.7<br>15.9 | 0.85 | 0.15 | 27.3 | 24.7 | 2.7 |
| M-MOF-808 | 1252 | 11.8<br>14.8 | 1.64 | 0.33 | 25.1 | 22.7 | 3.1 |

After the methanol activation, in-situ FTIR analysis was performed in order to observe changes in local structure of MOF-808, and the results are shown in FIGS. 6 to 9. Table 3 shows wave numbers indicating functional groups.

Figure 6:
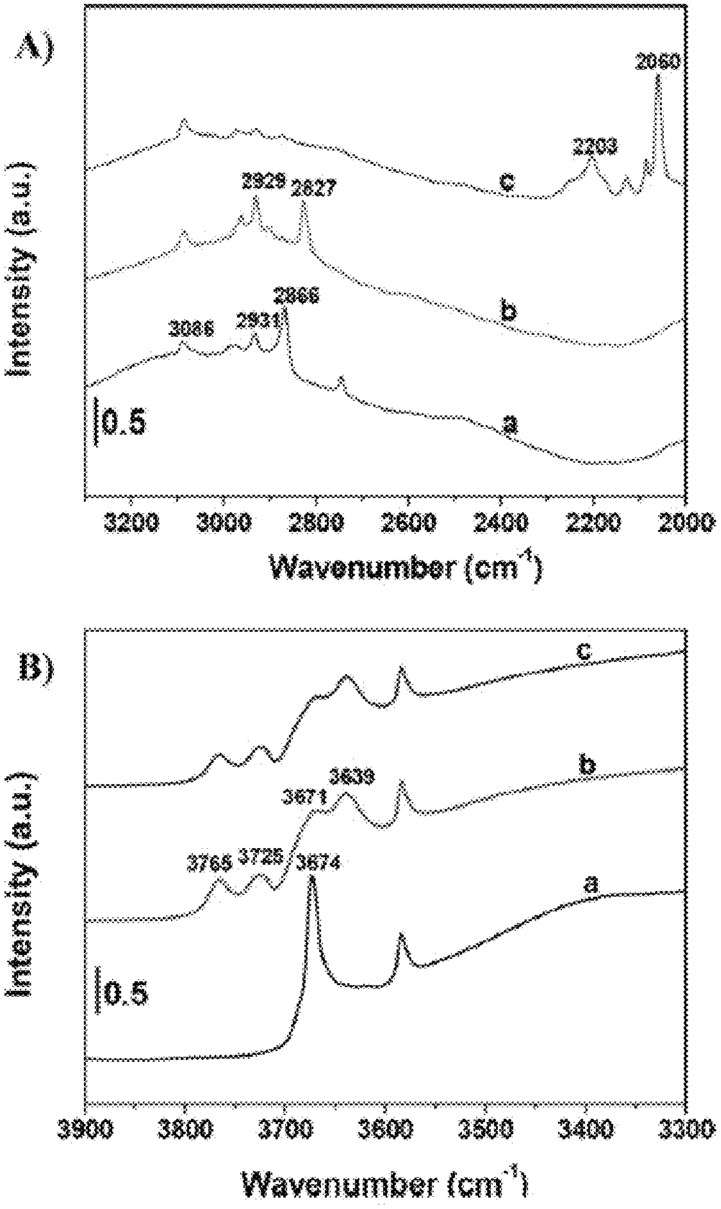
FIGS. 6 to 9 show the results of in-situ FTIR analysis for observing changes in local structure of MOF-808 after methanol activation.
Figure 7:
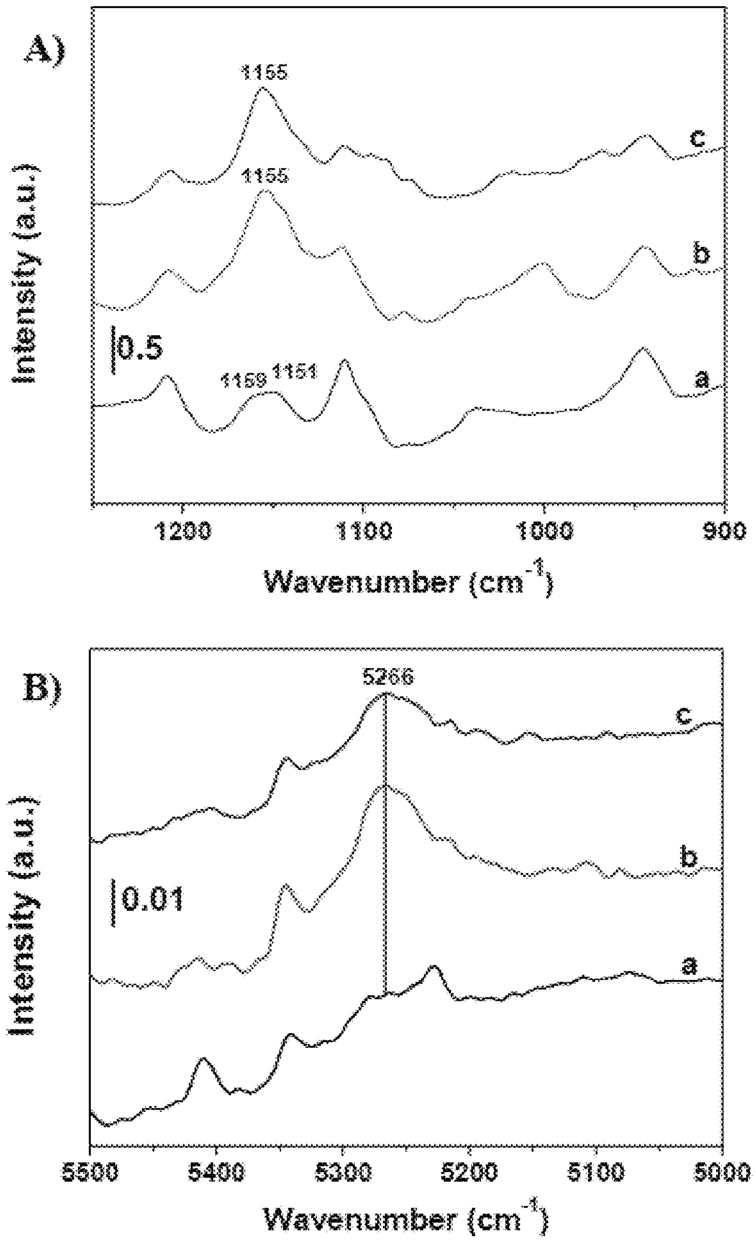
Figure 8:
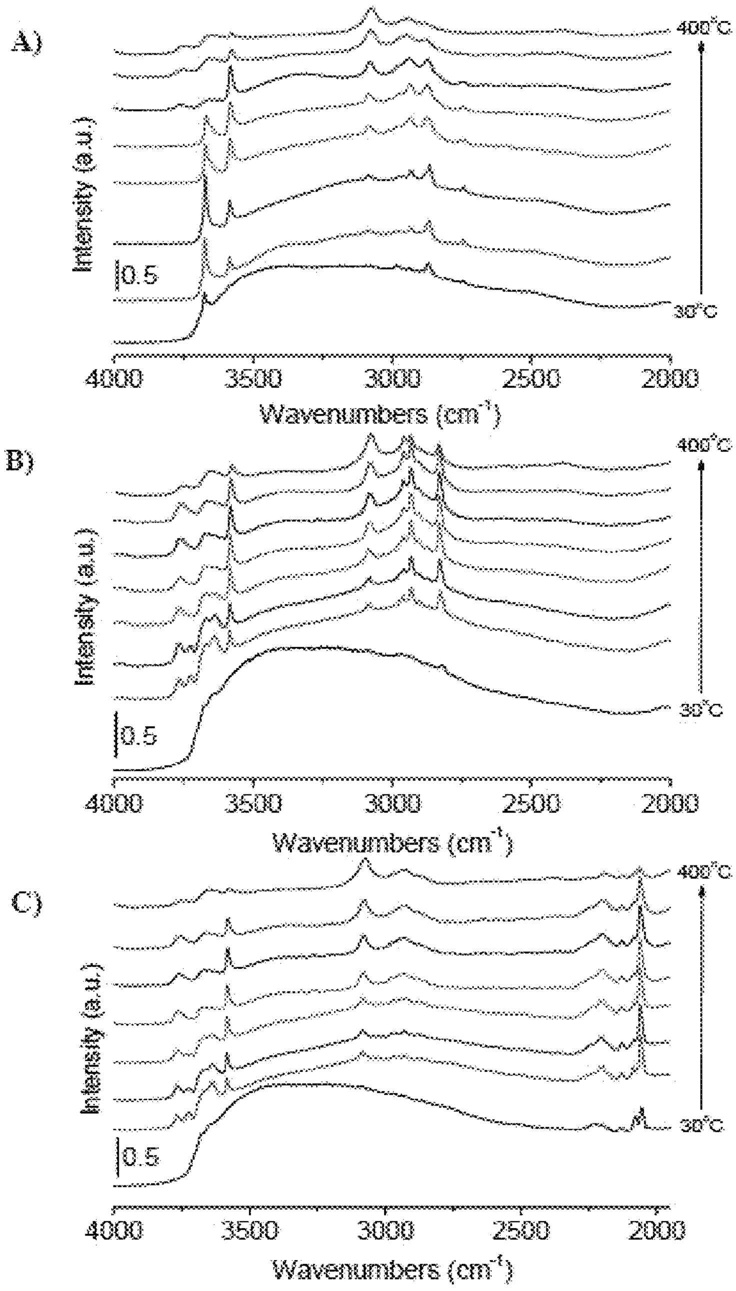
Figure 9:
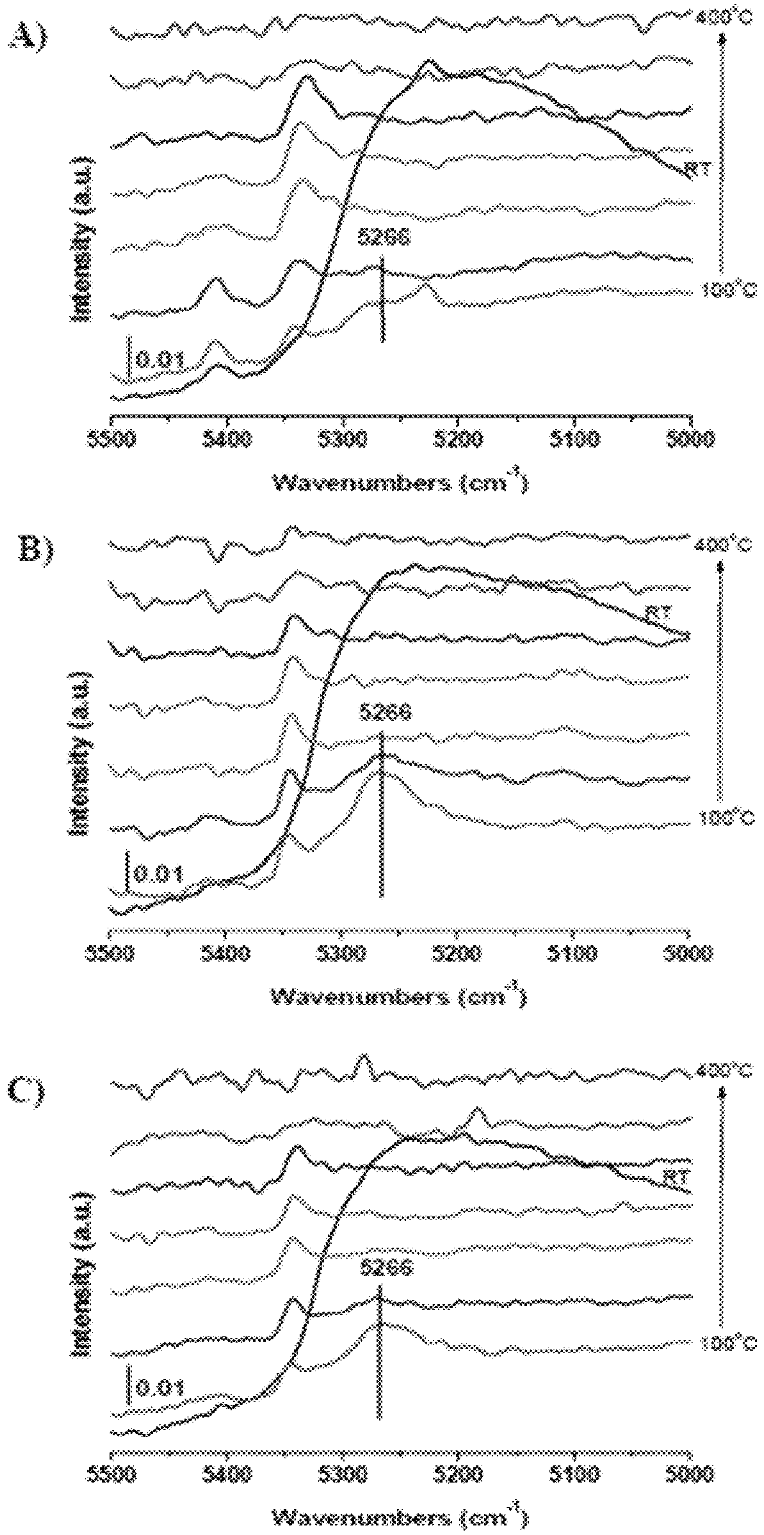

In the in-situ FTIR measurement, the sample was evacuated at 100° C. for 2 hours, and then the FTIR measurement was performed. FIGS. 6 and 7 show FTIR analysis at room temperature, in which a represents MOF-808, b represents M-MOF-808, and c represents d-M-MOF-808. FIGS. 8 and 9 show the results of the FTIR measurement performed at different temperatures, in which A shows the FTIR result of MOF-808, B shows the FTIR result of M-MOF-808, and C shows the FTIR result of d-M-MOF-808. The d-M-MOF-808 refers to a sample obtained by performing an activation-modifying reaction of the MOF-808 using $CD_3OD$ which is methanol substituted by deuterium.

TABLE 3

| Wavenumber ($cm^{-1}$) | Functional Group | Assignment |
|---|---|---|
| 3765 | O—H | Terminal O—H stretch (Zr—OH) |
| 3725 | | Water asymmetric stretch ($H_2O$—Zr) |
| 3674 | | Bridged $\mu_3$-OH stretch |
| 3671 | | Bridged $\mu_3$-OH stretch on new surface |
| 3639 | | Water asymmetric stretch ($H_2O$—Zr) |
| 5266 | | Bending + stretching mode ($H_2O$—Zr) |
| 2931 | C—H | C—H stretch of Zr—OOCH |
| 2929 | | C—H asymmetric stretch of Zr—$OCH_3$ |
| 2866 | | C—H stretch of Zr—OOCH |
| 2827 | | C—H symmetric stretch of Zr—$OCH_3$ |
| 2203 | C—D | C—D asymmetric stretch of Zr—$OCD_3$ |
| 2060 | | C—D symmetric stretch of Zr—$OCD_3$ |
| 1155 | C—O | C—OH stretch of Zr—$OCH_3$ |

In the case of the MOF-808 not modified with methanol, characteristic bands appear at 2931 $cm^{-1}$ and 2866 $cm^{-1}$, which means the C—H stretching vibration of the Zr-connected formate group (Zr—OOCH). On the other hand, in the case of the M-MOF-808, the C—H stretching vibration mode appears at replaced wave numbers of 2929 $cm^{-1}$ and 2827 $cm^{-1}$, which means Zr—$OCH_3$ in which a methoxy group is connected to Zr.

In order to confirm the grafting of the methoxy group on the Zr site, an isotopic exchange experiment was performed using $CD_3OD$ (deuterated methanol) containing deuterium.

Referring to this, the C—H stretching band from Zr—OOCH does not appear at all, and two new bands caused by Zr—$OCD_3$, in which the C-D stretching vibration of the deuterated methoxy group is connected to Zr, are observed at 2203 $cm^{-1}$ and 2060 $cm^{-1}$.

On the other hand, the peak appearing at 3086 $cm^{-1}$ indicates the C—H stretching of the aromatic group (BTC), which shows that there is no change by methanol activity.

Further, in the methanol-activated sample, a new C—O vibration peak is observed at 1155 $cm^{-1}$, showing that a Zr—O—C bond is formed in the MOF-808 activated by grafting alcohol moieties to the metal node (FIG. 7A).

The methanol activation process was not performed in an inert atmosphere, and the MOF-808 was exposed to atmospheric water before and after the activation (reflux) step.

Therefore, the substitution of some methoxy groups by OH groups may explain the existence of methoxy groups as well as terminal OH groups observed in FTIR analysis.

The peak of 3674 $cm^{-1}$ in the MOF-808 means bridging of the $\mu_3$-OH group. After the methanol activation (M-MOF-808), the peak disappears, and four new peaks are formed in the same region (FIG. 6B). Peaks at 3671 $cm^{-1}$ and 3765 $cm^{-1}$ represent $\mu_3$-OH stretches and non-hydrogen-bonded terminal OH groups on the newly formed surface, respectively.

Further, the remaining two peaks were present at 3725 $cm^{-1}$ and 3639 $cm^{-1}$, and were not observed along with the peak at 5266 $cm^{-1}$ after the sample was heated at 150° C. or higher (FIGS. 7 to 9). Therefore, the peak is deemed to correspond to a water molecule coordinated with the Zr site.

CO-FTIR Analysis of MOF-808 and M-MOF-808

Figure 10:
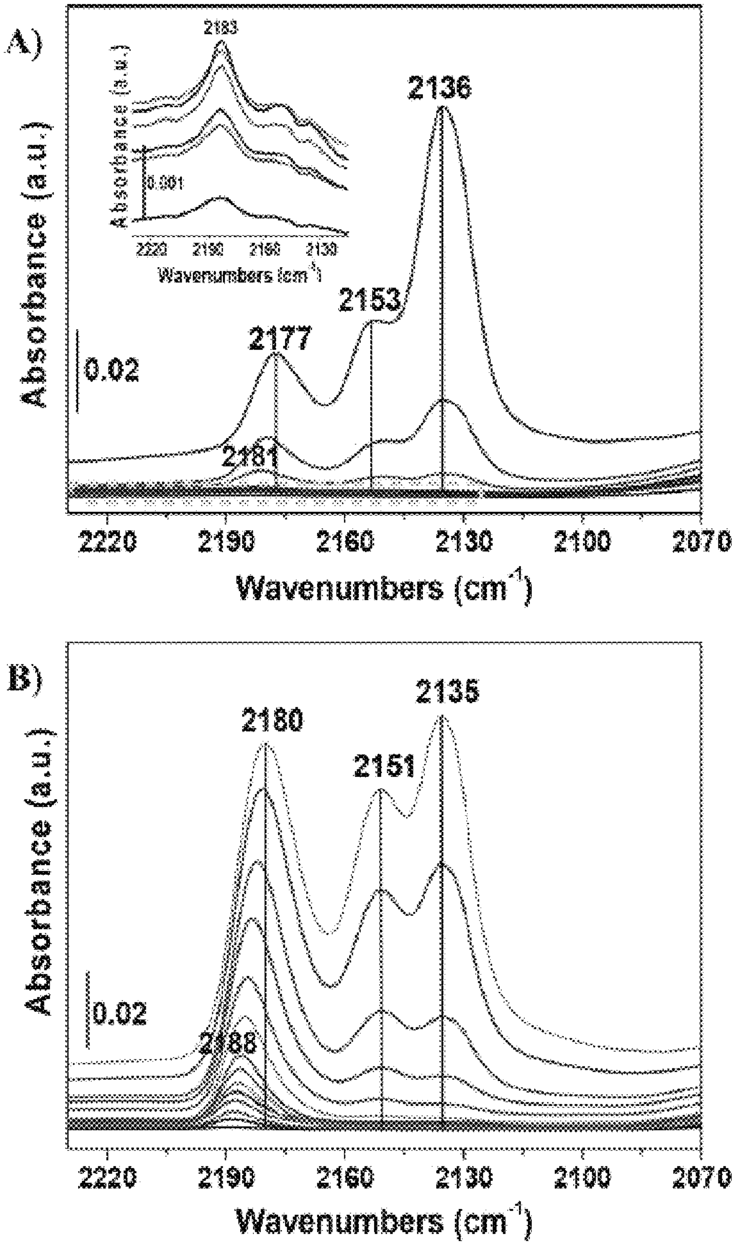
FIG. 10 shows the results of CO-FTIR analysis performed on MOF-808 and M-MOF-808.

FIGS. 10A and 10B show the CO-FTIR analysis performed on each of MOF-808 and M-MOF-808. This was performed to determine coordinativedly unsaturated Zr sites (Zr-CUS).

Further, the FTIR experiment was performed by injecting a measured amount of CO after the sample was activated at 150° C. for 6 hours to adsorb CO at −173° C.

In the case of the M-MOF-808, a v (CO) band centered at 2188 $cm^{-1}$ appeared, gradually expanded as the CO capacity was increased, and moved to a lower wave number of 2180 $cm^{-1}$. The peak is deemed to correspond to CO coordinated with a Lewis acid site (Zr-CUS).

The red shift of the peak indicates the possibility of the formation of multicarbonyl species in Zr-CUS. Only when the CO coverage is higher and the Zr-CUS site is saturated, two additional V(CO) bands appeared at 2151 $cm^{-1}$ and 2135 cm-1, corresponding to H-bonded CO molecules of $\mu_3$-OH and physically adsorbed CO molecules, respectively.

On the other hand, almost no peak was found in (pristine) MOF-808 before the modification, but a very small peak is seen when the initial spectrum located at 2183 $cm^{-1}$ is enlarged by twenty times in FIG. 10A. This peak is measured at the initial CO coverage, which indicates that the vacant Zr species is present in a negligible amount in the MOF-808.

Further, at the higher CO coverage, three v (CO) bands located at 2177 $cm^{-1}$, 2153 $cm^{-1}$, and 2136 $cm^{-1}$ appeared simultaneously. Further, the presence of H-bonded CO and physically adsorbed CO bands can be confirmed using peaks at 2153 $cm^{-1}$ and 2136 $cm^{-1}$, respectively.

Figure 11:
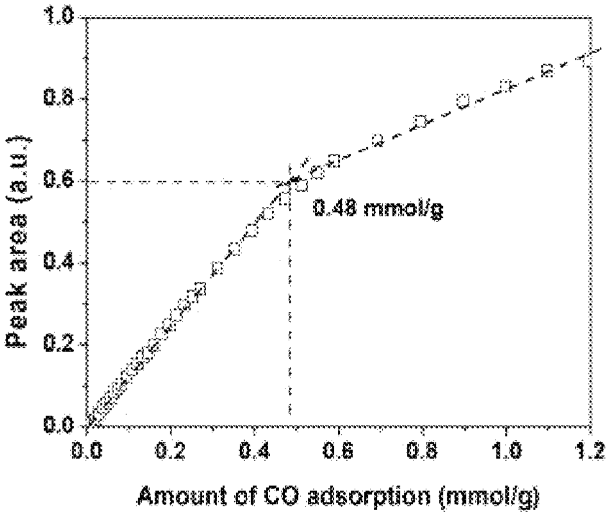
FIG. 11 is a graph obtained by quantifying the amount of Zr-CUS present in M-MOF-808 using a plot of 2188 $cm^{-1}$ peak area versus amount of CO adsorption.

As shown in FIG. 11, the amount of Zr-CUS present in M-MOF-808 was additionally quantified using a plot of 2188 $cm^{-1}$ peak area versus amount of CO absorption. The amount of chemical adsorption (chemisorption) of CO reached a maximum of 0.48 mmol/g, which confirmed was using a linear correlation between the peak area and the amount of CO absorption. Further, due to the physically adsorbed CO molecules, linearity was tented after the adsorption of 0.48 mmol/g of CO, which means that about 0.5 mmol/g of Zr-CUS was formed in the M-MOF-808 activated with methanol. This quantified value of Zr-CUS may be changed when the MOF-808 is synthesized under another reaction condition.

Hydrogenation Reaction of MOF-808 and M-MOF-808

The methanol activation of the MOF-808 may change the local structure thereof through the modification of the metal node, thus changing the chemical properties of the MOF-808. This modification of the local structure may be related to catalytic activity.

Figure 12:
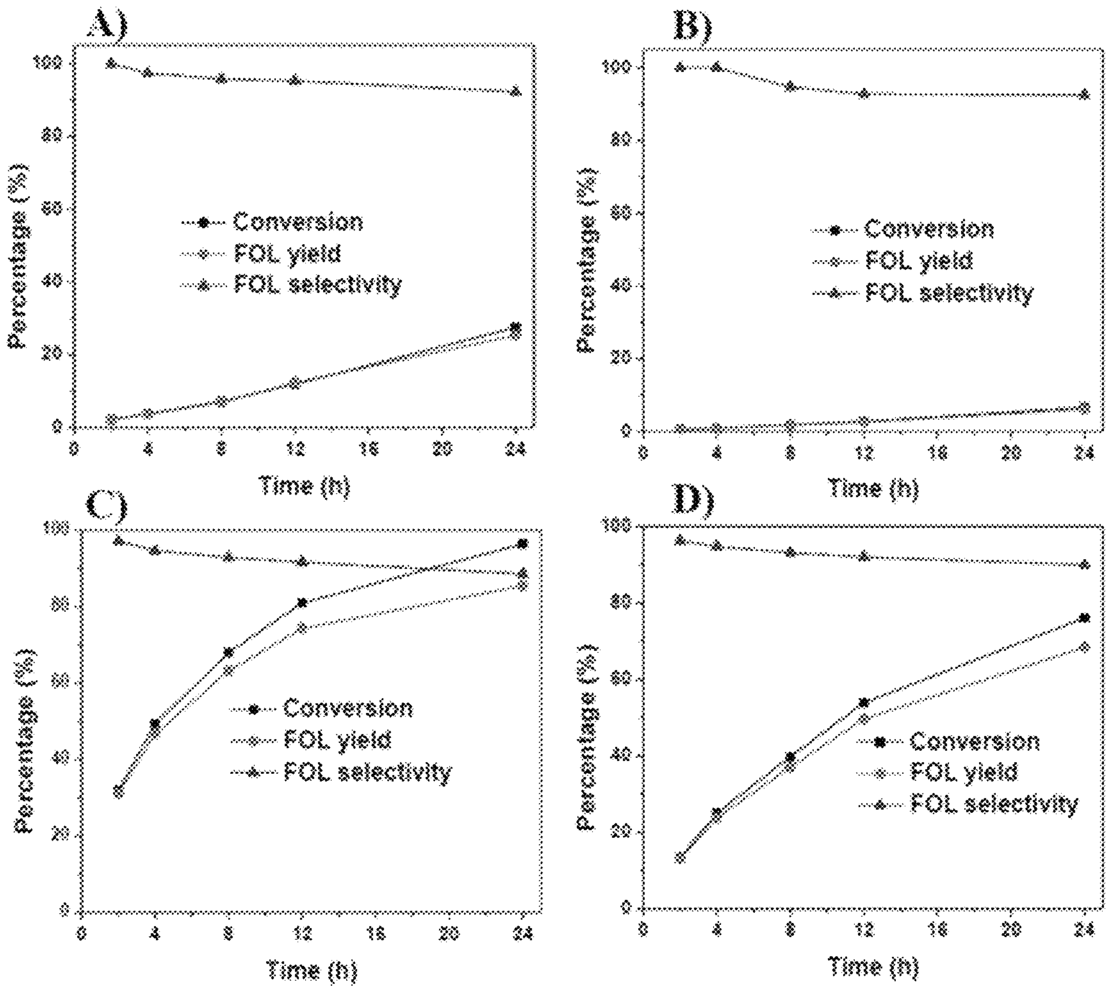
FIG. 12 shows the results of FUR conversion rate and FOL selectivity at 30° C. (B and D) and 40° C. (A and C) using MOF-808 and M-MOF-808.

Accordingly, a test was performed on the hydrogenation reaction from FUR to FOL using the MMOF-808 catalyst, and the results are shown in Table 4 (TOF (turnover frequency)–(mole of FOL)/(mole of "Zr" from ICP analysis× time) at reaction time of 2 h).

dramatic difference in activity can be observed. Further, at 30° C., the MOF-808 and the M-MOF-808 showed the conversion rate of 6.7% and 76.1% and the FOL selectivity of 6.2% and 68.5%, respectively. FIG. 12 shows the FUR conversion rate and FOL selectivity at 30° C. (B and D) and 40° C. (A and C). The reaction conditions in FIG. 12 are the results obtained from the reaction after mixing 0.5 g of FUR, 12.5 g of IPA, and 0.1 g of the catalyst. In FIG. 12, the MOF-808 was used as the catalyst in the case of FIGS. 12A and 12B, and the M-MOF-808 was used as the catalyst in the case of FIGS. 12C and 12D.

This remarkable improvement in catalytic activity of the M-MOF-808 may be attributed to the modified local structure of the M-MOF-808. In the MOF-808, the proton topology is changed by substituting formate groups with terminal OH and methoxy groups, and the formation of Zr-CUS improves the density of acid and base sites to promote adsorption of FUR and IPA on metal nodes, resulting in improved FUR conversion rate and FOL yield.

Figure 13:
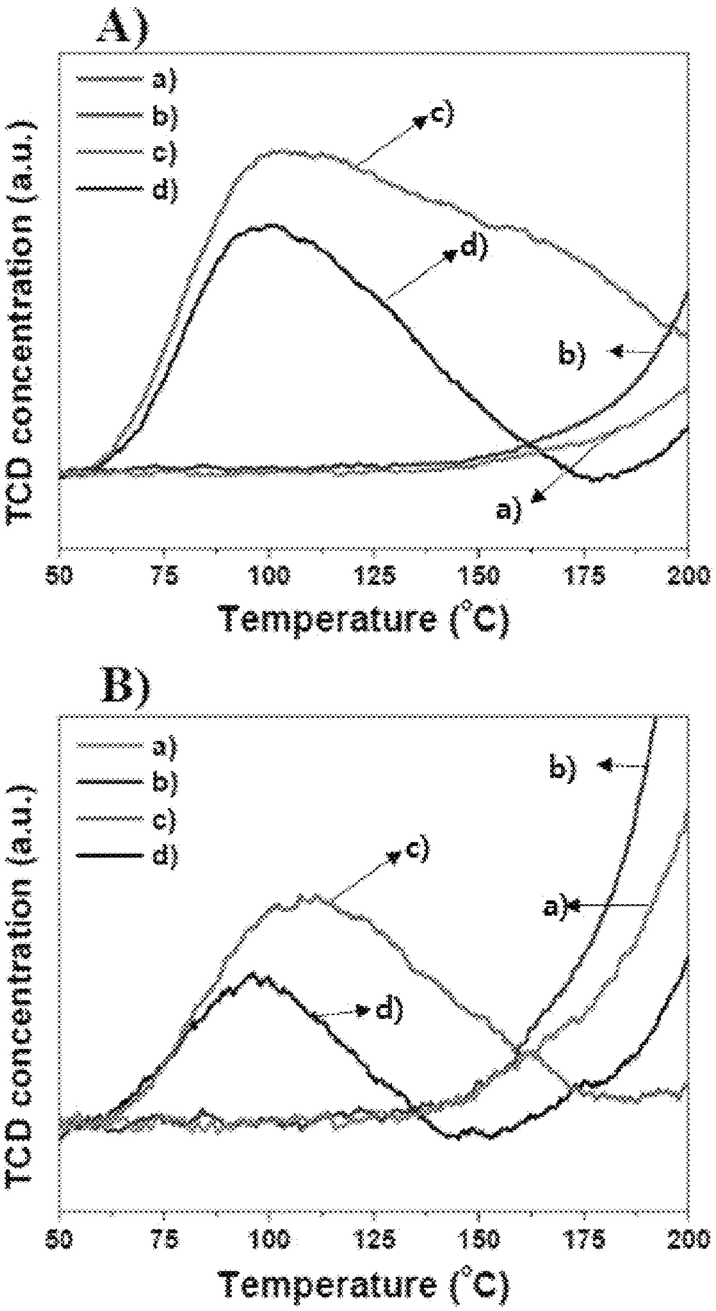
FIG. 13 shows the results of A) $NH_3$-TPD and B) $CO_2$-TPD for measuring the density of acid and base sites of MOF-808 and M-MOF-808.

FIG. 13 shows the results of A) $NH_3$-TPD and B) $CO_2$-TPD for measuring the density of acid and base sites of the MOF-808 and M-MOF-808. In FIG. 13, a shows the blank result of the M-MOF-808, b shows the blank result of the MOF-808, c shows the TPD result obtained after adsorption of $NH_3$ or $CO_2$ on the M-MOF-808, and d shows the TPD result obtained after adsorption of $NH_3$ or $CO_2$ on the MOF-808.

The MOF-808 modified with methanol exhibits significant reaction results even at 30° C. or 40° C. as described above. Therefore, when the M-MOF-808 is used as the catalyst, a large amount of low-grade waste heat generated in industrial processes is capable of being used, which is another merit of increasing energy efficiency. This makes it possible to provide eco-friendly and sustainable development routes of biomass-derived chemical materials.

The catalytic activity of the M-MOF-808 in the hydrogenation reaction of FUR was compared to the activity of other Zr-based catalysts.

TABLE 4

| No. | Catalyst | Temperature (° C.) | Time (h) | Mass ratio (Cat./FUR/IPA) | Conversion rate (%) | $Y_{FOL}$ (%) | $S_{FOL}$ (% ) | TOF ($h^{-1}$) |
|---|---|---|---|---|---|---|---|---|
| 1 | MOF-808 | 40 | 24 | 0.1/0.5/12.5 | 27.5 | 25.4 | 92.3 | 0.2 |
| 2 | M-MOF-808 | 40 | 24 | 0.1/0.5/12.5 | 96.5 | 85.5 | 88.6 | 2.9 |
| 3 | MOF-808 | 82 | 2 | 0.1/1/25 | 81.3 | 66.4 | 81.7 | 11.6 |
| 4 | M-MOF-808 | 82 | 2 | 0.1/1/25 | 89.3 | 79.1 | 88.6 | 15.0 |
| 5 | $Zr_6O_4$ $(OH)_4$ $(Mc)_{12}$ | 82 | 2 | 0.1/1/25 | 3 | 0.9 | 30 | 0.2 |
| 6 | $ZrO_2$ | 82 | 2 | 0.1/1/25 | 2.7 | 0.2 | 7.4 | 0.01 |
| 7 | ZrO $(OH)_2$ | 82 | 2 | 0.1/1/25 | 8.9 | 7.1 | 79.8 | 0.6 |
| 8 | DUT-67 | 82 | 2 | 0.1/1/25 | 16.4 | 13.5 | 82.3 | 2.0 |
| 9 | M-DUT-67 | 82 | 2 | 0.1/1/25 | 37.9 | 34.1 | 89.9 | 5.4 |
| 10 | M-MOF-808 | 100 | 2 | 0.1/1/25 | 99.2 | 93.0 | 93.8 | 17.6 |
| 11 | ZrPn | 100 | 15 | 0.1/0.24/7.9 | 93 | 90 | 96.8 | 3.1 |
| 12 | Zr-LS | 100 | 1 | 0.1/0.1/7.9 | 97.5 | 96 | 98.5 | 4.4 |
| 13 | Zr-FDCA | 140 | 4 | 0.1/0.19/7.9 | 83 | 78 | 94.0 | 2.7 |

Referring to Table 4, when the reaction is performed under a reflux condition at 82° C., the M-MOF-808 exhibits the higher FUR conversion rate and FOL selectivity compared to the MOF-808 synthesized under the same condition, but the difference is not significant. This is deemed to be because the conversion reaction of FUR to FOL at the above temperature is close to an equilibrium point.

However, after the reaction at a temperature of 40° C. for 24 hours, the MOF-808 showed the FUR conversion rate of only 27.5%, whereas the M-MOF-808 showed the FUR conversion rate of 96.5% under the same condition, so a A fully coordinated methyl acrylate (Mc) Zr cluster ($Zr_6O_4$ (OH) 4 (Mc) 12) as a homogeneous catalyst exhibited only a conversion rate of 3%, similar to the low activity of 12-connected Zr-MOFs, and $ZrO_2$ exhibited only a FOL yield of 0.2% and a low conversion rate of 2.7%. In the case of $ZrO(OH)_2$, the conversion rate was 8.9%, which was the improved catalytic activity compared to that of $ZrO_2$, and the FOL selectivity was excellent. This is because hydrouszirconia is capable of strongly activating alcohol as a proton donor through hydroxyl groups present on the surface of the catalyst, thereby promoting transferring of hydride ions. In contrast, calcined $ZrO_2$ exhibits lower catalytic activity because the number of hydroxyl groups is small.

The M-MOF-808 exhibited the performance better than that of all other catalysts in Table 4 with respect to the TOF. The M-MOF-808 exhibited a FOL yield of 93.3% as the temperature thereof was increased from 82° C. to 100° C., indicating reaching almost complete conversion (99.3%).

Other catalysts such as zirconium phosphonate, lignosulfonate, and carboxylate complexes also have activity to this reaction, and exhibit a quantitative yield of FOL. However, in the case of these catalysts, higher temperatures and larger amounts of catalysts were required compared to the MOF catalyst according to the present disclosure in order to reach the optimum yield of FOL.

Figure 14:
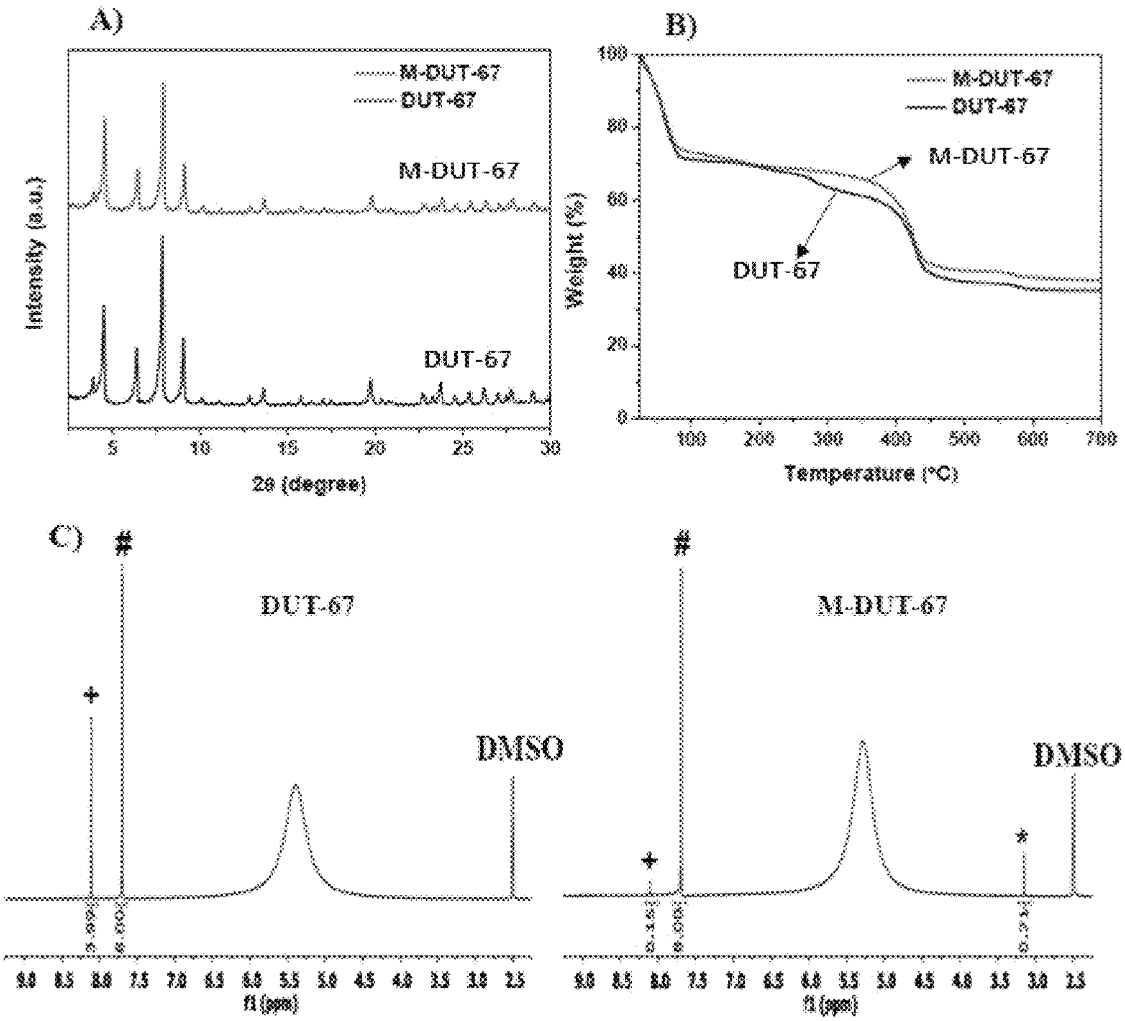
FIG. 14 shows the results of XRD, TGA, and 1H NMR analyses of DUT-67 modified with methanol.

In order to confirm whether the effect of methanol modification on the metal nodes of the MOFs according to the present disclosure is possible in MOFs other than MOF-808, DUT-67 (8-connected) was selected as other low-coordinated Zr-MOFs and activated using methanol. Upon the methanol 5 activation, DUT-67 exhibited the metal node modification similar to the case of the MOF-808 (FIG. 14), and the catalytic activity of the M-DUT-67 activated with methanol was significantly improved. FIG. 14A shows an XRD pattern, FIG. 14B shows a TGA result, and FIG. 14C shows a 1H NMR pattern. In FIG. 14C, the MOFs were digested in HF/DMSO-d6, #denotes TDC, +denotes formate, and * denotes methanol.

Figure 15:
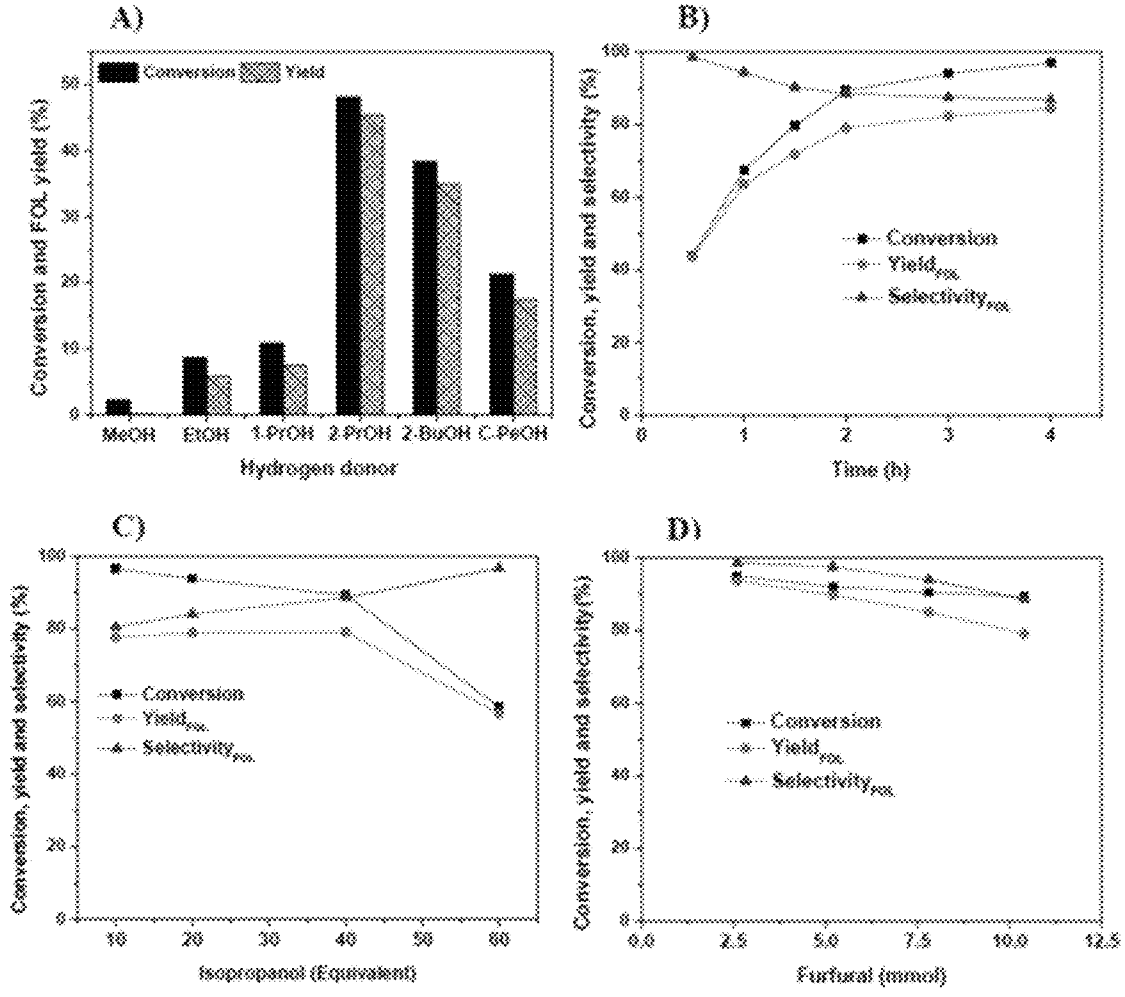
FIG. 15 shows the results of the experiment for optimizing reaction parameters proton such as a donor/solvent, a reaction time, and the concentrations of IPA and FUR for M-MOF-808.

FIG. 15 shows the results of the experiment for optimizing reaction parameters such as a proton donor/solvent, a reaction time, and the concentrations of IPA and FUR.

In FIG. 15, the optimization of the reaction parameters in the hydrogenation reaction of FUR to FOL using the M-MOF-808 under a reflux condition was performed. FIG. 15A shows the effect of the proton donor on the hydrogenation reaction of FUR to FOL over the M-MOF-808. The reaction was performed at a temperature of 65° C. for 2 hours under a reaction condition including 1.0 g (10.4 mmol) of FUR, 25 g (416 mmol) of IPA, and 0.1 g of the catalyst. FIG. 15B shows the effect of reaction time under a condition including 1.0 g (10.4 mmol) of FUR, 25 g (416 mmol) of IPA, 0.1 g of the catalyst, and refluxing at a reaction temperature of 82° C. FIG. 15C shows the effect of IPA concentration. This effect is the result obtained from the reaction including 1.0 g (10.4 mmol) of FUR over 0.1 g of the catalyst with reflux at a reaction temperature of 82° C. for 2 hours. FIG. 15D shows the effect of FUR concentration. This effect is the result obtained from the reaction including 25 g (416 mmol) of IPA over 0.1 g of the catalyst with reflux at a temperature of 82° C. for 2 hours.

In FIG. 15A, various primary and secondary alcohols were screened to investigate the effect of the hydrogen donor. For the purpose of rational comparison, an experiment was performed while the reaction temperature was set to the lowest boiling point of methanol among the tested Primary alcohols such as methanol, ethanol, and 10 alcohols. 1-propanol exhibited the low conversion of FUR. Meanwhile, secondary alcohols, especially 2-propanol, exhibited excellent performance with a FUR conversion rate of 48.1% and a FOL yield of 45.5%. This is deemed to be due to the difference in the reduction potential of the primary alcohols and the secondary alcohols. In the case of the secondary the activity was increased as the hydrogen donor molecule became small. Further, cyclopentanol, which is a cyclic secondary alcohol, exhibited the poorest performance among the used secondary alcohols. This is deemed to be because steric hindrance occurs around the carbonyl group, which makes it difficult to perform adjustment with the catalytically active metal node moieties, and thus cyclopentanol has a lower activity than larger secondary alcohol. Therefore, 2-propanol was used as the hydrogen donor in the subsequent reaction.

The effect of the reaction time was investigated using 2-propanol as the solvent and the hydrogen donor. As shown in FIG. 15B, after the reaction time of 30 minutes, the conversion rate of FUR reached about 45% with almost 100% selectivity for FOL. The conversion rate of up to 89% was obtained after 2 hours, but the FOL selectivity was slightly reduced. This reduction in FOL selectivity is deemed to be due to two main competing side reactions including the reaction of IPA and FUR and the aldol condensation of acetone and FUR. 4 hours were required for FUR conversion of 97.0%, and the FOL selectivity was further reduced to 86.9%. Therefore, in consideration of an appropriate FUR conversion rate and FOL selectivity, a reaction time of 2 hours was selected in the subsequent reaction experiment.

FIG. 15C shows the effect of the IPA concentration (molar equivalent to FUR) on the FUR conversion and FOL selectivity. A conversion of 96.5% was achieved when the IPA concentration was 10 equivalents to FUR. However, the selectivity for FOL was reduced (80.5%) due to acetal formation and aldol condensation of side reactions which were competitive. As the IPA concentration in the reaction medium was increased, side reactions were suppressed, and the FOL selectivity was improved up to 90% when 40 equivalents of IPA were used. As the IPA concentration was further increased to 60 equivalents, the reaction proceeded very slowly and the FUR conversion of about 60% was achieved. The selectivity for FOL was highest 93.7% at this concentration, which is deemed to be due to the low FUR conversion and high IPA concentration. Accordingly, it can be seen that the side reactions are suppressed through the use of a higher IPA concentration and that an optimum concentration is required to maintain a high conversion rate with appropriate FOL selectivity.

FIG. 15D shows the effect of an initial concentration of FUR on the FOL yield and selectivity. When the initial concentration of FUR was in the range of 10.4 to 2.6 mmol, the FUR conversion and FOL yield were continuously increased. At the initial concentration of FUR of 2.6 mmol, the FUR conversion rate of 95% was obtained with the FOL selectivity of 99.1%. This indicates that by reducing a ratio of FUR to the catalyst, almost quantitative FUR conversion rate and FOL selectivity are obtained within the reaction time of 2 hours.

From this, IPA was used as the hydrogen donor to reach the maximum FOL yield (yield of 94.1% with selectivity of 99.1% under a reflux condition for a reaction time of 2 hours). Optimization may be performed by changing the IPA and initial FUR concentrations at 30° C. to achieve the quantitative yield and high selectivity of FOL. After a reaction time of 24 hours, the maximum FOL yield was 90% (FOL selectivity of 94.2%).

Figure 16:
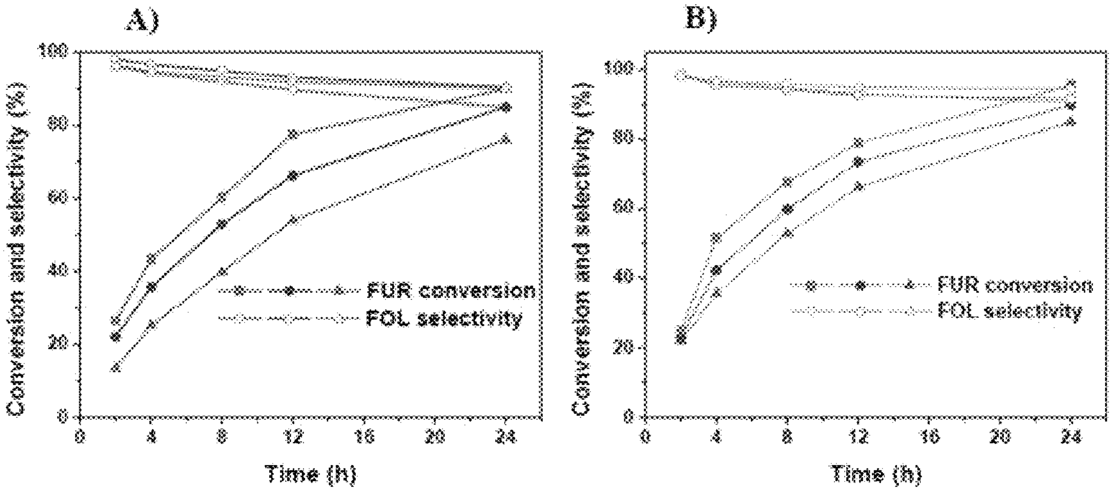
FIG. 16 shows the results of the experiment for optimizing reaction parameters in the hydrogenation reaction of FUR to FOL using M-MOF-808 at 30° C.

FIG. 16 shows the results of the experiment for optimizing reaction parameters in the hydrogenation reaction of FUR to FOL using M-MOF-808 at 30° C. FIG. 16A shows the effect of the IPA concentration. In the graph of FIG. 16A, red represents 10 equivalents, blue represents 20 equivalents, green represents 40 equivalents, and the reaction condition includes 0.5 g (5.2 mmol) of FUR and 0.1 g of the catalyst. FIG. 16B shows the effect of the FUR concentration, red represents 1.3 mmol, blue represents 2.6 mmol, and green represents 5.2 mmol. The reaction condition includes 6.25 g (104 mmol) of IPA and 0.1 g of the catalyst.

FIG. 16A shows the effect of an IPA concentration on FUR conversion and FOL selectivity at 30° C. It can be seen that the hydrogenation of FUR under a reflux condition follows the previously mentioned trend. When the IPA concentration was increased from 10 equivalents to 20 equivalents (with respect to FUR), the FOL selectivity was gently improved from 85% to 90%. However, when the concentration is further increased up to 40 equivalents, the FOL selectivity does not change noticeably, and the conversion rate is reduced from 84.9% to 76%. This result shows that the IPA concentration is increased to suppress side reactions, but it can be seen that the further increase of the IPA concentration (more than 20 equivalents) makes the reaction proceed slowly without a significant change in FOL selectivity. Therefore, in order to maintain a high conversion rate with appropriate FOL selectivity, an IPA concentration of 20 equivalents was selected as the optimal IPA concentration.

FIG. 16B shows the effect of an initial concentration of FUR on FOL selectivity at a reaction temperature of 30° C. When the initial concentration of FUR was reduced from 5.2 mmol to 1.3 mmol, the FUR conversion rate and FOL selectivity were continuously increased. When the initial concentration of FUR is 1.3 mmol, the FOL selectivity of 94.2% and the FUR conversion rate of 95.5% are obtained. This shows that almost quantitative FUR conversion rate and FOL selectivity are obtained at room temperature within a reaction time of 24 hours by reducing a ratio of the FUR concentration to the catalyst.

Figure 17:
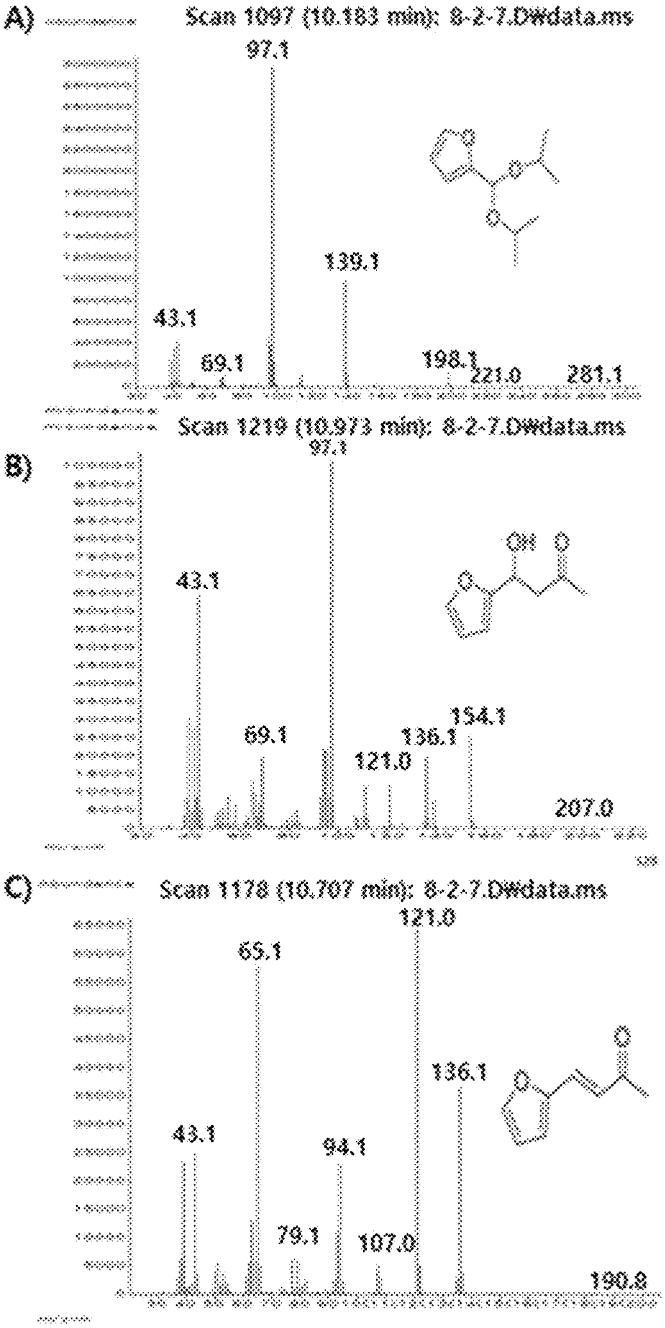
FIG. 17 shows the result of analysis of the main by-products of the reaction using GC-MS.
Figure 18:
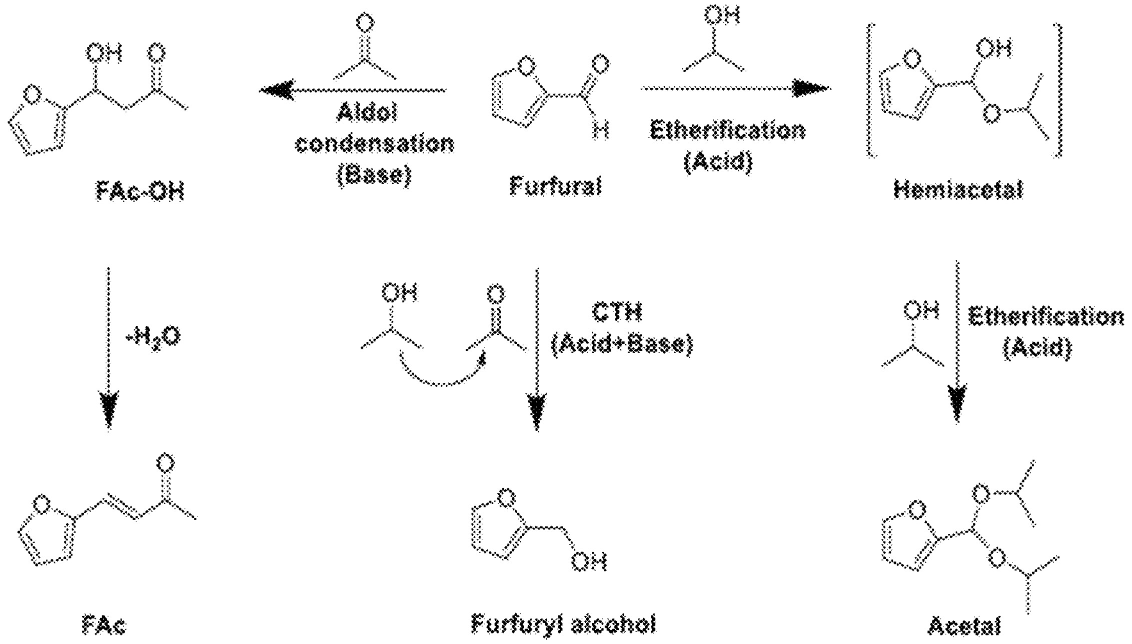
FIG. 18 is a suggested reaction mechanism of FUR to FOL.

The main by-products of the reaction were analyzed using GC-MS (FIG. 17), and a valid reaction mechanism obtained therefrom is shown in FIG. 18. FOL was quantitatively generated from FUR and IPA through a hydrogenation reaction mechanism. Diisopropyl methyl furfural (DIPMF), which is commonly referred to as acetal, is formed by reacting FUR and IPA at acid sites. Further, acetone formed from IPA after the donation of two protons undergoes an aldol condensation reaction with FUR in the presence of a base site to form 4-(2-furyl)-4-hydroxybutan-2-one (FAc-OH) and 4-(2-furyl)-3-buten-2-one (FAc). It has been reported that acetal formation and aldol condensation side reactions during the hydrogenation reaction of the carbonyl group are associated with acid and base sites.

Reuse of Catalyst (1) Possibility of Filtration of Catalyst

In order to confirm the possibility of filtration of the catalyst, the M-MOF-808 catalyst was used. After 1 hour, two parallel experiments were performed, in which the catalyst was separated from the high-temperature reaction mixture and was not separated therefrom, as shown in FIG. 19A.

After agitation for 4 hours under the same condition, the conversion from FUR to FOL using the M-MOF-808 was continuously performed, but when the catalyst was filtered after 1 hour, the reaction hardly proceeded. The result of inductively coupled plasma (ICP) analysis showed that both filtrates did not contain "Zr" species. Thereby, the heterogeneous character of the M-MOF-808 catalyst was confirmed in the hydrogenation reaction of FUR.

(2) Catalytic Activity of Reused Catalyst

Figure 19:
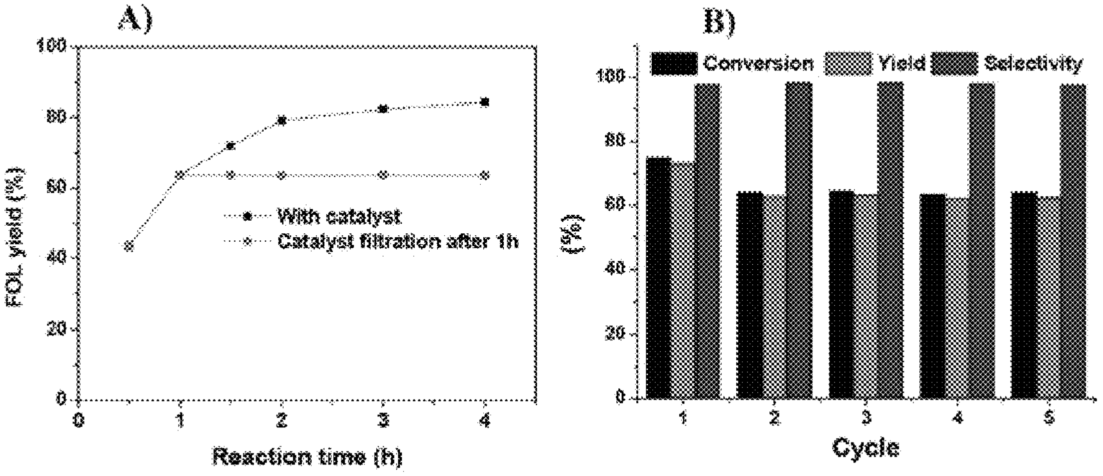
FIG. 19 shows the results of two parallel experiments in which an M-MOF-808 catalyst is separated from a reaction mixture and is not separated from the reaction mixture.

With respect to the reusability of the M-MOF-808 catalyst, in order to clearly observe the change in the catalytic activity, an experiment was conducted under the optimum reaction condition with a low conversion rate, as shown in FIG. 19B.

The conversion rate was about 75% in a first cycle, but was reduced to 64% in a second cycle, resulting in a slight reduction in catalytic activity in the second cycle. However, in subsequent catalytic cycles, the conversion rate remained stable at about 64%, and the FOL selectivity remained above 97% in all cycles.

This shows that some of the active sites of the catalyst may be blocked after the first cycle due to a small amount of substrate or the formed molecules having strong interactions with the catalyst surface.

Figure 20:
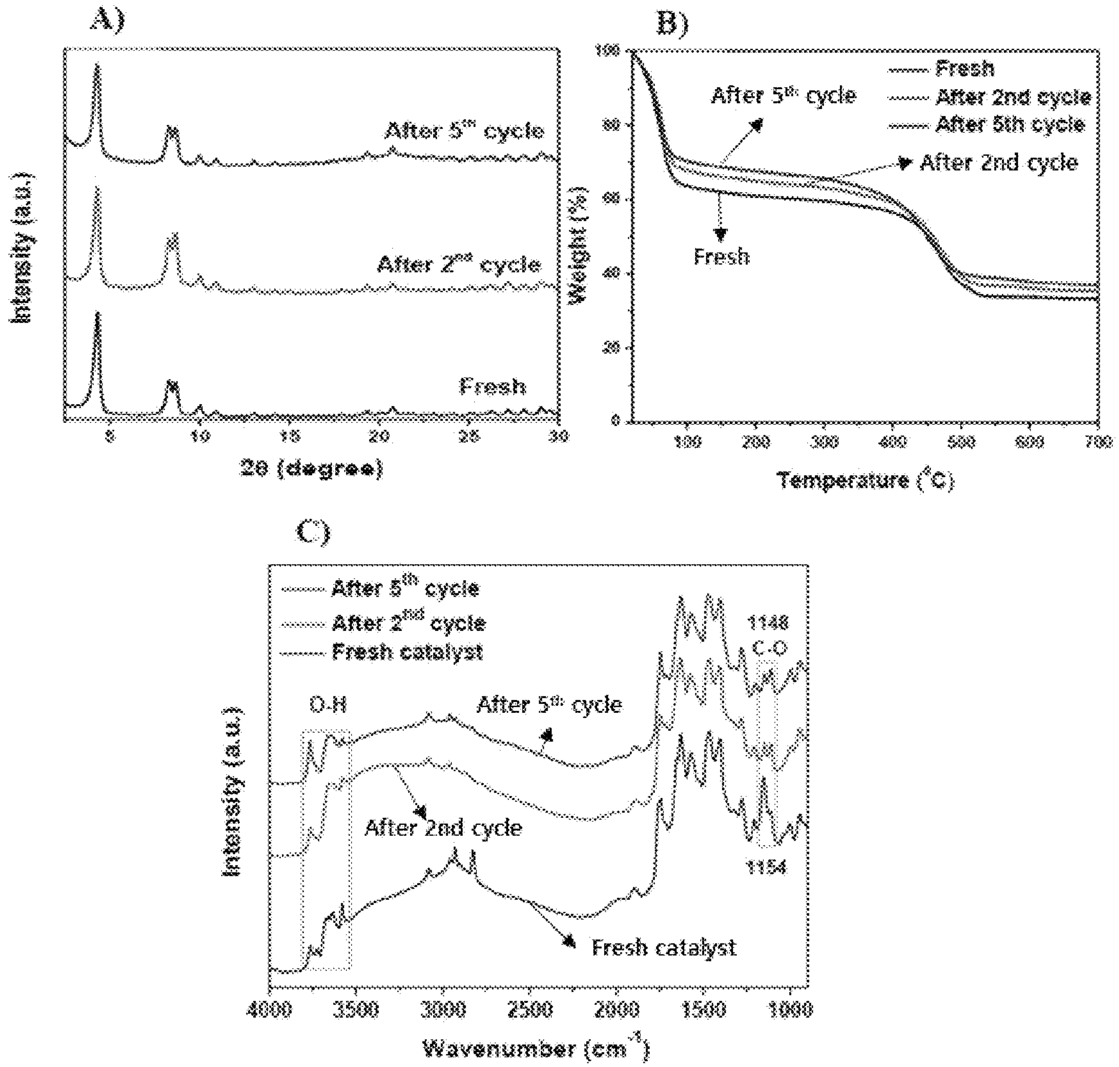
FIG. 20 shows the results of PXRD, TGA, and in-situ FTIR analyses for observing the structural change in M-MOF-808 after use.
Figure 21:
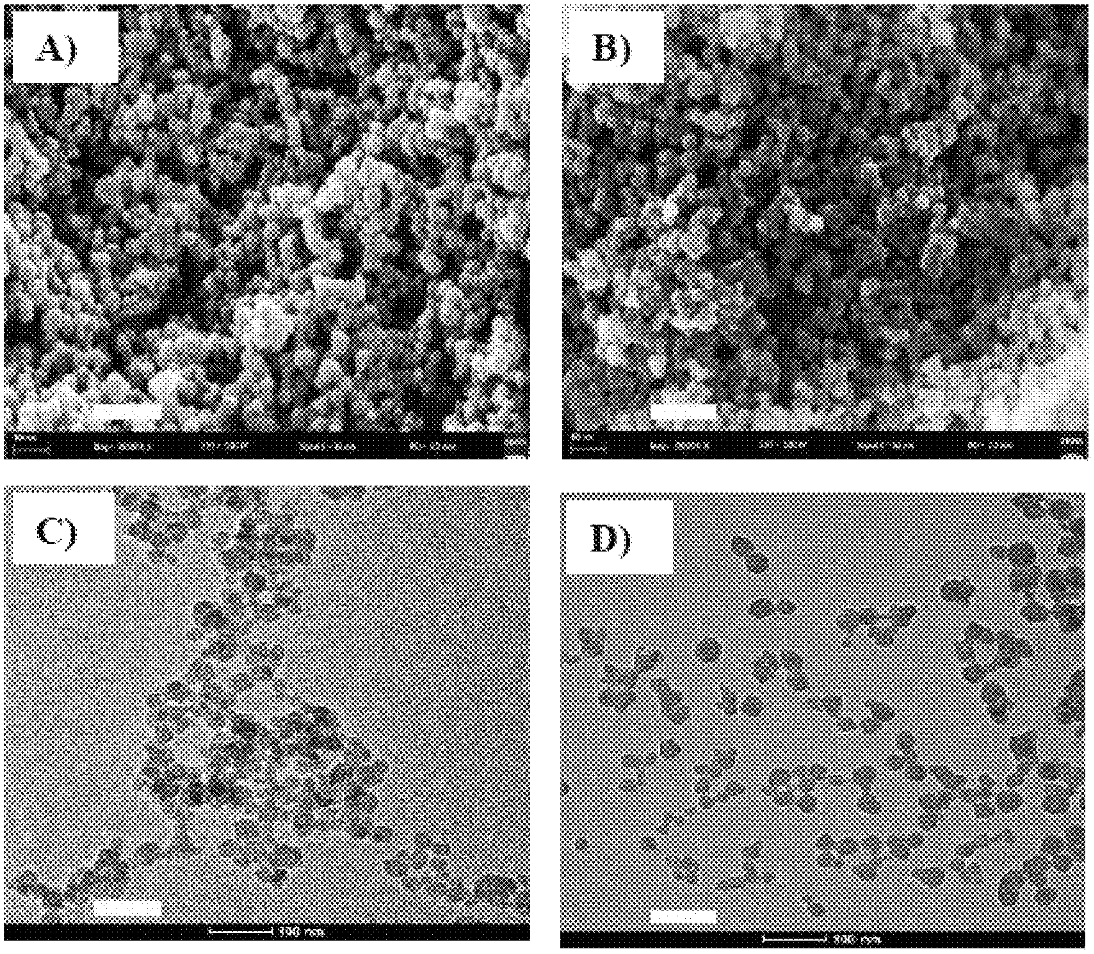
FIG. 21 shows the results of SEM and TEM analyses.

In order to observe the structural change in M-MOF-808 after use, analysis was performed using PXRD, TGA, in-situ FTIR, SEM, and TEM, and the results are shown in FIGS. 20 and 21.

FIG. 20A shows the PXRD pattern of the fresh and used M-MOF-808 catalysts, FIG. 20B shows the TGA curve, and FIG. 20C shows the FTIR results measured at room temperature after evacuation at 150° C. for 2 hours. FIGS. 21A and 21B show SEM images of the fresh catalyst and the catalyst reused five times, and FIGS. 21C and 21D show TEM images of the fresh catalyst and the catalyst reused five times, respectively.

All crystalline peaks in the PXRD pattern of the catalyst used were maintained without a change in intensity (FIG. 20A). Although the thermal stability of the catalyst was maintained (FIG. 20B), the catalyst that was used tended to be decomposed earlier compared to an initial catalyst, and exhibited a slightly more weight loss compared to the fresh catalyst before use at 250 to 400° C. This is deemed to be related to the decomposition of the organic moiety deposited on the catalyst surface. The catalyst that was used exhibited a slightly less weight loss compared to the fresh catalyst at t 100° C. or lower because pores were partially covered with the deposited organic species formed during the reaction to thus reduce the adsorption rate of water molecules in the pores of the M-MOF-808. Referring to the in-situ FTIR results of FIG. 20C, the OH peaks (3725 $cm^{-1}$ and 3639 $cm^{-1}$) corresponding to the water molecules coordinated with the Zr site did not appear in the catalyst FTIR patterns after the second and fifth cycles (FIG. 20C), and the peaks at 2929 $cm^{-1}$, 2827 $cm^{-1}$, and 1154 $cm^{-1}$ related to the C—H and C—O stretching of Zr—$OCH_3$ were significantly reduced. Further, in the fresh catalyst, the C—O stretching frequency shifts from 1154 $cm^{-1}$ to 1148 $cm^{-1}$. This is deemed to be because, in the case of the catalyst, the $OCH_3$ groups on the Zr-surface and the coordinated water molecules are replaced by the organic moiety from the reaction system after the first cycle. Nevertheless, in consideration of the size of the peak at 1148 $cm^{-1}$, it is believed that the organic moiety is present in a small amount. In FIG. 21, as confirmed by the comparison of SEM and TEM images of the fresh catalyst and the used catalyst, the shape of the particles was maintained even after the five recycling tests.

<Range of Substrate>

In addition to the hydrogenation reaction of FUR, the activity of the MOF catalyst according to the present disclosure was measured for hydrogenation reactions using various substrates. A hydrogenation reaction experiment was performed using representative aldehydes and ketones and other biomass-derived carbonyl compounds as the range of the substrate, and the results are shown in Table 5 below (reaction condition: 2.6 mmol of the substrate, 416 mmol of IPA, 0.1 g (10.6 mol %) of the catalyst, and a temperature of 82° C. (reflux)).

TABLE 5

| No. | Substrates | Products | Time (h) | Conversion rate (%) | Yield (%) | Selectivity (%) | TOF ($h^{-1}$) |
|---|---|---|---|---|---|---|---|
| 1 | 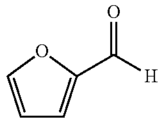 | 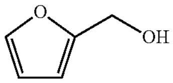 | 2 | 95 | 94.1 | 99.1 | 4.4 |
| 2 | 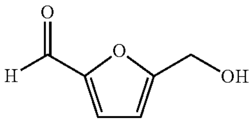 | 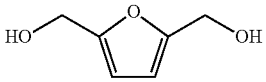 | 2 | 98.2 | 96.2 | 98.0 | 4.6 |
| 3 | 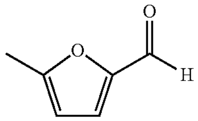 | 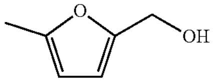 | 6 | 95.0 | 88.0 | 92.6 | 1.4 |
| 4 | 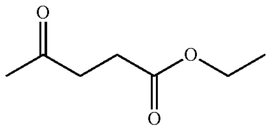 | 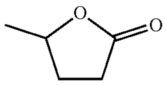 | 24 | 90.7 | 82.8 | 91.3 | 0.3 |
| 5 | 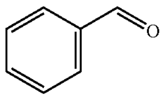 | 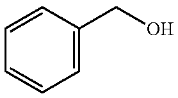 | 1 | 93.1 | 93.1 | 100 | 8.8 |
| 6 | 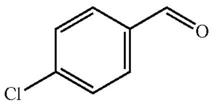 | 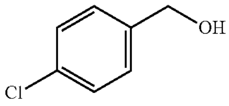 | 1 | 97.0 | 97.0 | 100 | 9.2 |
| 7 | 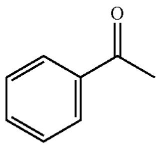 | 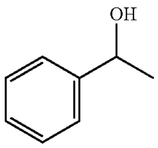 | 8 | 92.5 | 92.5 | 100 | 1.1 |

All carbonyl compounds tested in Table 5 above are effectively catalyzed by the M-MOF-808 to produce alcohols corresponding thereto in high yield. However, it can be seen that a longer reaction time is required in the hydrogenation reaction of ketones (Nos. 4 and 7).

Further, the M-MOF-808 catalyst may promote the hydrogenation transfer from 5-hydroxymethylfurfural (HME), which is an important biomass-derived platform chemical material, to 2,5-bis-(hydroxymehtyl) furan (BHMF) with a high selectivity of 98% (No. 2).

When a methyl group is introduced at position 5 of FUR (5-MF), the reaction time required to achieve a conversion rate (95%) similar to that of FUR is increased to 6 hours. This is because the electron density for the C atom of the carbonyl group is increased due to the electron-donating property of the methyl group to thus interrupt the reaction of the hydride ion to the carbonyl carbon. Further, a slowdown in reaction speed due to steric hindrance may be another factor.

In contrast, it is shown that the electron withdrawing group attached to the aromatic ring at the para position serves to improve the speed of the hydrogenation reaction (Nos. 5 and 6).

In order to explain the performance of the M-MOF-808 in the transfer hydrogenation reaction near room temperature, the same carbonyl described in Table 5 was used and the hydrogenation reaction was performed at 30° C. The results are shown in Table 6.

The reaction condition in Table 6 below includes 1.3 mmol of the substrate, 104 mmol of IPA, 0.1 g (21.2 mol %) of the catalyst, and a reaction temperature of 30° C. After the reaction, the products were separated by column chromatography on silica gel (hexane:acetone of 65:35), and the yield of the separated product is shown in parentheses.

TABLE 6

| No. | Substrates | Products | Time (h) | Conversion rate (%) | Yield (%) | Selectivity (%) | TOF ($h^{-1}$) |
|---|---|---|---|---|---|---|---|
| 1 | 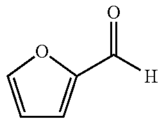 | 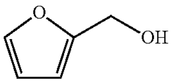 | 24 | 95.5 | 90 | 94.2 | 0.2 |
| 2 | 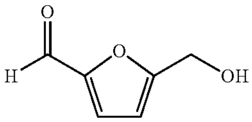 | 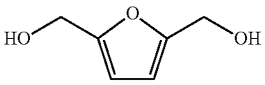 | 24 | 97.1 | 96.1 (90) | 99 | 0.2 |
| 3 | 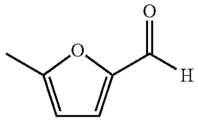 | 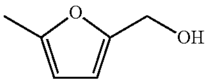 | 24 | 67.9 | 61.4 | 90.4 | 0.1 |
| 4 | 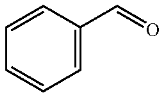 | 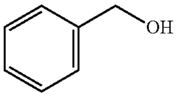 | 5 | 90 | 90 (86) | 100 | 0.9 |
| 5 | 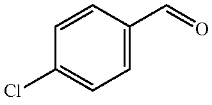 | 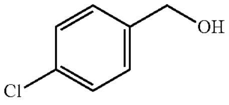 | 5 | 99.3 | 95.5 | 96.2 | 0.9 |
| 6 | 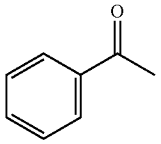 | 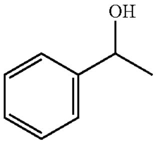 | 48 | 55.8 | 55.8 | 100 | 0.05 |

As shown in Table 6, all substrates may be efficiently promoted by the M-MOF-808 to generate the corresponding alcohol in high yield, and serve to effectively convert HMF into BHMF with a high selectivity of 99.0% even at 30° C. In the same manner as in Table 5, when the methyl group was introduced into FUR at a position of 5 (5-MF), it was observed that the conversion rate of the substrate was sharply reduced to 67.9%. In contrast, the electron-withdrawing group attached to the aromatic ring at the para position significantly improved the speed of the hydrogenation reaction, and a longer reaction time was required for the hydrogenation reaction of the ketone (item 6). The methyl group attached to the carbonyl carbon may cause steric hindrance, contributing to the slowing of the reaction speed, and even after the reaction for 48 hours, only 55.8% of acetophenone was converted into each alcohol with selectivity of 100%. However, as in the reaction at a reaction temperature of 82° C., complete conversion of acetophenone was achieved without a reduction of the selectivity of the product. These results show that the M-MOF-808 has great utility as a catalyst for the hydrogenation reaction in both organic synthesis and biomass conversion at a temperature close to room temperature using the M-MOF-808.

Table 7 below shows an experiment for hydrogenation of the M-MOF-808 catalyst when the substrate is a, β-unsaturated carbonyl. The reaction condition of Table 7 below was the same as that of Table 6, except that the reaction temperature was 82° C. In the table below, the type of the central metal of MOF-808 was set to Zr or Hf.

TABLE 7

| Substrates | Products | Cat. (M-Zr and HF) | Time (h) | Conv. (%) | Sel. (%) |
|---|---|---|---|---|---|
| 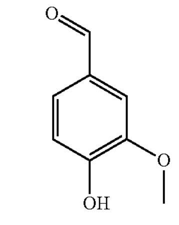 Vanillin | 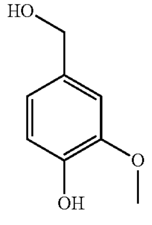 Vanillyl alcohol | Zr | 5 | 92.4 | 100 |
| | | Hf | 5 | 96.9 | 100 |
| 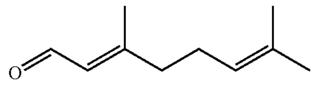 Citral | 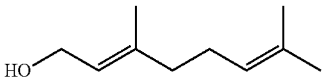 Geraniol/Nerol | Zr | 2 | 98.7 | 96.8 |
| | | Hf | 2 | 99.6 | 97.9 |
| 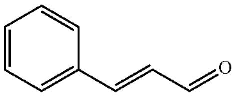 Cinnamaldehyde | 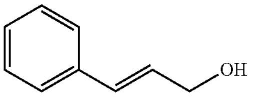 Cinnamyl alcohol | Zr | 2 | 99.1 | 96.2 |
| | | Hf | 2 | 99.4 | 97.9 |
| 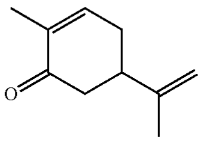 Carvone | 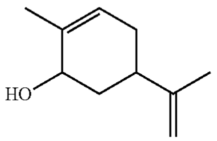 Carveol | Zr | 1 | 9.8 | 100 |
| | | Hf | 1 | 18.8 | 97.9 |
| | | Zr | 8 | 68.1 | 100 |
| | | Hf | 8 | 72.9 | 99.6 |

Effects of Types of Alcohol for Modifying MOF

Table 8 shows the results of an experiment of the hydrogenation reaction from FUR to FOL while changing the type of alcohol when the MOF-808 is modified.

TABLE 8

| Entry | Catalyst* | T ° C. | t (H) | Mass Ratio (g) Cat/FUR/IPA | Conv, (%) | $Y_{FOL}$ (%) | $S_{TOL}$ (%) | TOF ($h^{-1}$) |
|---|---|---|---|---|---|---|---|---|
| 1 | MOF-808 | 82 | 2 | 0.1/1/25 | 81.3 | 66.4 | 81.7 | 11.6 |
| 2 | M-MOF-808 | 82 | 2 | 0.1/1/25 | 89.3 | 79.1 | 88.6 | 15.0 |
| 3 | E-MOF-808 | 82 | 2 | 0.1/1/25 | 87.4 | 76.5 | 87.5 | 13.1 |
| 4 | P-MOF-808 | 82 | 2 | 0.1/1/25 | 82.1 | 73.9 | 90.0 | 13.1 |
| 5 | MOF-808 | 40 | 24 | 0.1/0.5/12.5 | 17.7 | 16.0 | 90.4 | 0.1 |
| 6 | M-MOF-808 | 40 | 24 | 0.1/0.5/12.5 | 97.3 | 87.7 | 90.1 | 0.7 |
| 7 | E-MOF-808 | 40 | 24 | 0.1/0.5/12.5 | 90.6 | 80.7 | 89.1 | 0.6 |
| 8 | P-MOF-808 | 40 | 24 | 0.1/0.5/12.5 | 68.6 | 63.0 | 91.8 | 0.5 |

As shown in Table 8, it can be confirmed that when the MOF-808 is immersed in ethanol or propanol to be activated, the activity is lower than that of methanol but the yield is higher than that of pristine MOF-808 which is not activated.

Figure 22:
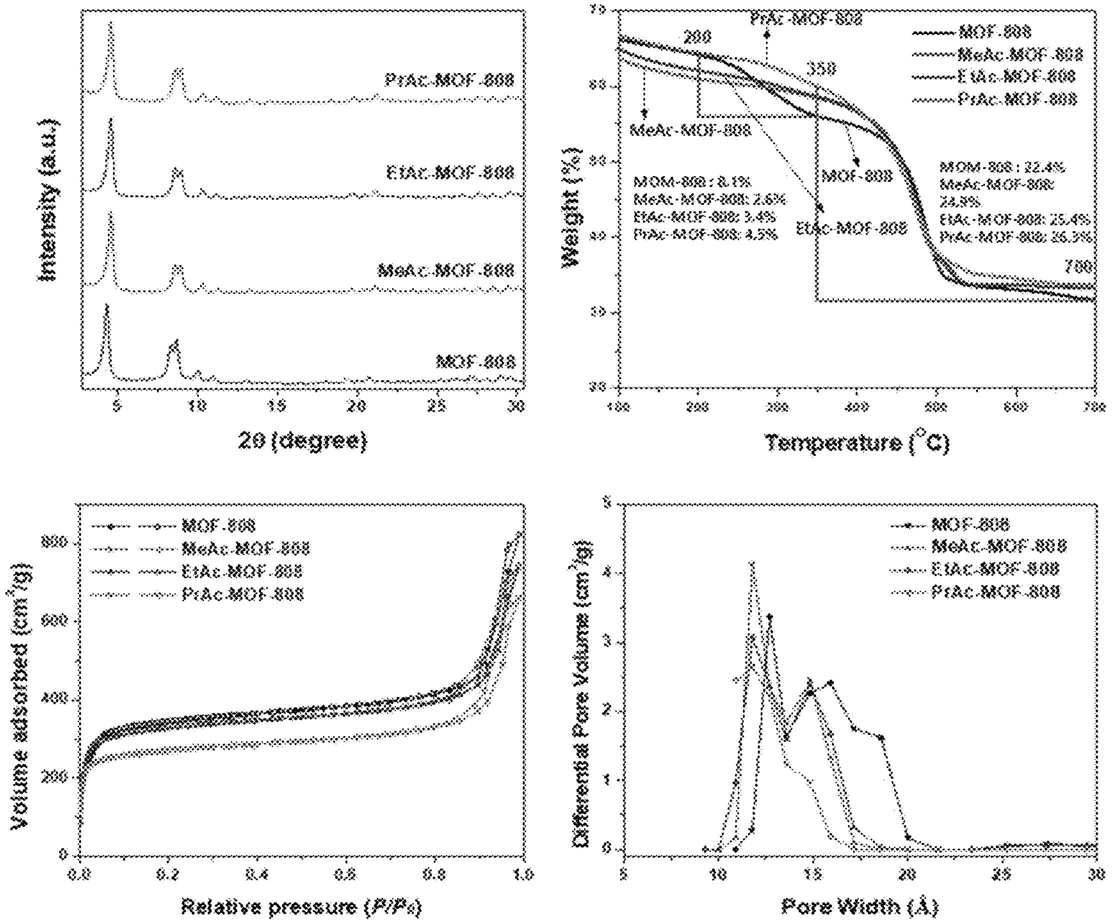
FIG. 22 is a graph obtained by performing PXRD, TGA, and $N_2$-physical adsorption analyses of the M-MOF-808 catalyst activated by immersion in ethanol and propanol.

FIG. 22 shows the results of PXRD, TGA, and $N_2$-physical adsorption analyses of the catalyst activated by immersion in ethanol and propanol.

In FIG. 22, MeAc means the case where activation is performed using methanol, EtAc means the case where activation is performed using ethanol, and PrAc means the case where activation is performed using propanol.

The present disclosure has been described above with reference to the accompanying drawings and embodiments, but this is only exemplary, and those of ordinary skill in the art will understand that various modifications and equivalent other embodiments are possible therefrom. Therefore, the technical protection scope of the present disclosure should be determined by the following claims.

What is claimed is:

1. A catalyst for a transfer hydrogenation reaction, comprising:

a metal-organic framework modified with one or more selected from among methanol, ethanol, and propanol, wherein the metal-organic framework has a metal node coordination number 8 or less, and wherein the catalyst is modified by a method comprising:

immersing the metal-organic framework in one or more alcohols selected from among methanol, ethanol, and propanol to manufacture a mixture;

performing refluxing while heating the mixture to or above a boiling point of the one or more alcohols selected from among methanol, ethanol, and propanol; and filtering, washing, and drying the modified metal-organic framework after the refluxing.

2. The catalyst for a transfer hydrogenation reaction of claim 1, wherein the metal-organic framework has a metal node coordination number of 10 or less.

3. The catalyst for a transfer hydrogenation reaction of claim 1, wherein the metal-organic framework is represented by Chemical Formula 1 or Chemical Formula 2 below:

$M_6O_{4+x}(OH)_m(BTC)_2(OR)_n$ [Chemical Formula 1]

M is a Group 4A or 4B element on a periodic table or a lanthanide-based metal having an oxidation state of $4^+$, x is greater than 0, a sum of m and n is 10 or less, m is greater than n, and R is an alkyl group having 1 to 10 carbon atoms $$M_6(\mu_3\text{-}O)_4(\mu_3\text{-}OH)_4(OH)_x(H_2O)_6(BTC)_2(OR)_y$$ [Chemical Formula 2]

x is any number greater than 0 and less than or equal to 12, y is any number from 0 to 6, M is a Group 4A or 4B element or a lanthanide-based metal having an oxidation state of $4^+$, and R is an alkyl group having 1 to 10 carbon atoms.

4. A method of producing a reduced organic compound, the method comprising:

performing a transfer hydrogenation reaction between an organic compound substrate and a hydrogen donor using the catalyst according to claim 1, wherein the organic compound substrate possesses functional group which is selected from among aldehyde and ketone.

5. A method of producing a reduced organic compound, the method comprising:

performing a transfer hydrogenation reaction between an organic compound substrate and a hydrogen donor using the catalyst according to claim 2, wherein the organic compound substrate possesses functional group which is selected from among aldehyde and ketone.

6. A method of producing a reduced organic compound, the method comprising:

performing a transfer hydrogenation reaction between an organic compound substrate and a hydrogen donor using the catalyst according to claim 1, wherein the organic compound substrate possesses functional group which is selected from among aldehyde and ketone.

7. A method of producing a reduced organic compound, the method comprising:

performing a transfer hydrogenation reaction between an organic compound substrate and a hydrogen donor using the catalyst according to claim 3, wherein the organic compound substrate possesses functional group which is selected from among aldehyde and ketone.

8. The method of claim 4, wherein the organic compound substrate is a compound represented by Chemical Formula 3 below:

[Chemical Formula 3]

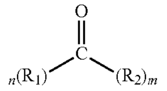

in Chemical Formula 3, $R_1$ and $R_2$ are the same or different, and are each independently an alkyl group having 1 to 10 carbon atoms substituted or unsubstituted by at least one substituent group selected from the group consisting of a hydroxy group, an alkyl group having 1 to 10 carbon atoms, an alkoxy group having 1 to 10 carbon atoms, an alkenyl group having 2 to 10 carbon atoms, an aryl group having 6 to 20 carbon atoms, a cycloalkyl group having 3 to 10 carbon atoms, a heterocyclic group having 2 to 10 carbon atoms, a carbonyl group having 1 to 10 carbon atoms, and a carboalkoxy group having 1 to 10 carbon atoms; an alkenyl group having 2 to 10 carbon atoms substituted or unsubstituted by at least one substituent group selected from the group consisting of a hydroxy group, an alkyl group having 1 to 10 carbon atoms, an alkoxy group having 1 to 10 carbon atoms, an aryl group having 6 to 20 carbon atoms, a cycloalkyl group having 3 to 10 carbon atoms, a heterocyclic group having 2 to 10 carbon atoms, a carbonyl group having 1 to 10 carbon atoms, and a carboalkoxy group having 1 to 10 carbon atoms; an aryl group having 6 to 20 carbon atoms substituted or unsubstituted by at least one substituent group selected from the group consisting of a halogen group, a hydroxy group, an alkyl group having 1 to 10 carbon atoms, an alkenyl group having 2 to 10 carbon atoms, and an alkoxy group having 1 to 10 carbon atoms; a heterocyclic group having 2 to 20 carbon atoms, which has at least one heteroatom selected from the group consisting of N, O, and S groups and which is substituted or unsubstituted by at least one substituent group selected from the group consisting of an alkyl group having 1 to 10 carbon atoms and an alkoxy group having 1 to 10 carbon atoms; hydrogen; a halogen group; or a hydroxy group, $R_1$ and $R_2$ are connected to each other to form a ring, and n and m are each independently an integer of 0 to 5.

9. The method of claim 4, wherein the organic compound substrate is at least one selected from among furfural, levulinic acid, 5-hydroxymethylfurfural (HMF), glycerol, fructose, glucose, 5-methyl furfural, butyl levulinate (BL), 1-(hydroxyethyl)benzene (1-HB), 7-keto-LCA (7-ketone-lithocholic acid), vanillin, citral, cinnamic aldehyde, carvone, ethyl levulinate, benzaldehyde, 4-chlorobenzaldehyde, acetophenone, and levulinic acid (LA).

10. The method of claim 4, wherein the hydrogen donor is petroleum-based alcohol or biomass-based alcohol.

* * * * *